(12) United States Patent
van Duzer et al.

(10) Patent No.: US 7,494,991 B2
(45) Date of Patent: *Feb. 24, 2009

(54) RIFAMYCIN ANALOGS AND USES THEREOF

(75) Inventors: John H. van Duzer, Georgetown, MA (US); Arthur F. Michaelis, Devon, PA (US); William B. Geiss, Athens, NY (US); Douglas G. Stafford, Niskayuna, NY (US); Xiang Y. Yu, Acton, MA (US); James M. Siedlecki, Burlington, MA (US); Yingfei Yang, Belmont, MA (US)

(73) Assignee: ActivBiotics Pharma, LLC, Tucker, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/804,141

(22) Filed: May 17, 2007

(65) Prior Publication Data

US 2007/0238747 A1    Oct. 11, 2007

Related U.S. Application Data

(63) Continuation of application No. 11/008,597, filed on Dec. 9, 2004, now Pat. No. 7,220,738.

(60) Provisional application No. 60/528,733, filed on Dec. 10, 2003.

(51) Int. Cl.
*C07D 498/14* (2006.01)
*C07D 491/14* (2006.01)
*A61K 31/542* (2006.01)
*A61K 31/498* (2006.01)
*A61P 31/04* (2006.01)

(52) U.S. Cl. ............... 514/219; 514/224.5; 514/229.5; 540/456

(58) Field of Classification Search ........... 540/456; 514/219, 224.5, 229.5
See application file for complete search history.

(56) References Cited

U.S. PATENT DOCUMENTS

| | | | |
|---|---|---|---|
| 3,338,888 A | 8/1967 | Bickel et al. | |
| 4,690,919 A | 9/1987 | Yamane et al. | |
| 4,859,661 A | 8/1989 | Kano et al. | |
| 4,965,261 A | 10/1990 | Kano et al. | |
| 4,983,602 A | 1/1991 | Yamane et al. | |
| 5,547,683 A | 8/1996 | Yano et al. | |
| 5,786,349 A | 7/1998 | Yamashita et al. | |
| 5,981,522 A | 11/1999 | Yamashita et al. | |
| 6,316,433 B1 | 11/2001 | Rose et al. | |
| 6,486,161 B1 | 11/2002 | Fujii et al. | |
| 6,566,354 B1 | 5/2003 | Rose et al. | |
| 6,900,204 B2 | 5/2005 | Michaelis et al. | |
| 2003/0203903 A1 | 10/2003 | Rose et al. | |
| 2003/0236265 A1 | 12/2003 | Sayada | |
| 2004/0014749 A1 | 1/2004 | Michaelis et al. | |
| 2004/0014750 A1 | 1/2004 | Michaelis et al. | |
| 2004/0034021 A1 | 2/2004 | Michaelis et al. | |
| 2004/0063718 A1 | 4/2004 | Michaelis et al. | |
| 2004/0077533 A1 | 4/2004 | Sayada | |
| 2004/0106590 A1 | 6/2004 | Eisenstein | |

FOREIGN PATENT DOCUMENTS

| | | |
|---|---|---|
| JP | 58-225093 | 12/1983 |
| JP | 59-231092 | 12/1984 |
| JP | 61-022090 | 1/1986 |
| JP | 62-240688 | 10/1987 |
| JP | 62-242687 | 10/1987 |
| JP | 63-035578 | 2/1988 |
| JP | 63-035579 | 2/1988 |
| JP | 63-233987 | 9/1988 |
| WO | WO 97/09047 | 3/1997 |
| WO | WO 2005/020894 | 3/2005 |
| WO | WO 2005/062882 | 7/2005 |

OTHER PUBLICATIONS

Bermudez et al., "Activity of KRM 1648 Alone or in Combination with Ethambutol or Clarithromycin Against *Mycobacterium avium* in Beige Mouse Model of Disseminated Infection," *Antimicrobial Agents and Chemotherapy* 38(8):1844-1848 (1994).

Dhople, "In Vivo Susceptibility of *Mycobacterium ulcerans* to KRM-1648, A New Benzoxazinorifamycin, in Comparison with Rifampicin," *Arzneimittelforschung* 51(6):501-505 (2001).

Dietze et al., "Safety and Bactericidal Activity of Rifalazil in Patients with Pulmonary Tuberculosis," *Antimicrobial Agents and Chemotherapy* 45(7):1972-1976 (2001).

Emori et al., "Evaluation of in Vivo Therapeutic Efficacy of a New Benzoxazinorifamycin, KRM-1648, in SCID Mouse Model for Disseminated *Mycobacterium avium* Complex Infection," *International Journal of Antimicrobial Agents* 10(1):59-65 (1998).

Fujii et al., "In Vitro and In Vivo Antibacterial Activities of KRM-1648 and KRM-1657, New Rifamycin Derivatives," *Antimicrobial Agents and Chemotherapy* 38:1118-1122 (1994).

Gidoh et al., "Bactericidal Action at Low Doses of a New Rifamycin Derivative, 3'-hydroxy-5'-(4-isobutyl-1-piperazinyl) Benzoxazinorifamycin (KRM-1648) on *Mycobacterium leprae* Inoculated into Footpads of Nude Mice," *Leprosy Review* 63(4):319-328 (1992).

(Continued)

*Primary Examiner*—Bruck Kifle
(74) *Attorney, Agent, or Firm*—David Bradin; Intellectual Property/Technology Law

(57) ABSTRACT

The present invention features rifamycin analogs that can be used as therapeutics for treating or preventing a variety of microbial infections. In one form, the analogs are acetylated at the 25-position, as is rifamycin. In another form, the analogs are deacetylated at the 25-position. In yet other forms, benzoxazinorifamycin, benzthiazinorifamycin, and benzdiazinorifamycin analogs are derivatized at various positions of the benzene ring, including 3'-hydroxy analogs, and/or various fused ring systems with the benzene ring at the 4',5' or 5',6' positions.

21 Claims, 10 Drawing Sheets

OTHER PUBLICATIONS

Heep et al., "Detection of Rifabutin Resistance and Association of rpoB Mutations with Resistance to Four Rifamycin Derivatives in *Helicobacter Pylori*," *European Journal of Clinical Microbiology& Infectious Diseases* 21:143-145 (2002).

Hirata et al., "In Vitro and In Vivo Activities of the Benzoxazinorifamycin KRM-1648 Against Mycobacterium Tuberculosis," *Antimocrobial Agents and Chemotherapy* 39(10):2295-2303 (1995).

Hosoe et al., "Identification and Antimicrobial Activity of Urinary Metabolites of a Rifamycin Derivative in Dog," *Xenobiotica* 26(3):321-332 (1995).

Hosoe et al., "Pharmacokinetics of KRM-1648, a new benzoxazinorifamycin, in Rats and Dogs," *Antimicrobial Agents and Chemotherapy* 40(12):2749-2755 (1996).

Ji et al., "How Effective is KRM-1648 in Treatment of Disseminated *Mycobacterium avium* Complex Infections in Beige Mice?," *Antimicrobial Agents and Chemotherapy* 40(2):437-442 (1996).

Kelly et al., "Low-Dose Aerosol Infection Model for Testing Drugs for Efficacy Against Mycobacterium Tuberculosis," *Antimicrobial Agents and Chemotherapy* 40(12):2809-2812 (1996).

Klemens et al., "Activity of KRM-1648 in Combination with Isoniazid Against Mycobacterium Tuberculosis in a Murine Model," *Antimicrobial Agents and Chemotherapy* 40(2):298-301 (1996).

Kump et al., "Zur Kenntnis von Rifamycin-S. Reaktionen des chinoiden Nucleus. Modifikationen von Antibiotica, 9. (Understanding of Rifamycin S. Reactions of the quinoid nucleus. Modifications of Antibiotics. 9)" *Helvetica Chimica Acta* 56(7):2348-2377 (1973). [English Abstract].

Kuo et al., "A Comparison of the In-Vitro Sensitivity of Chlamydia Pneumoniae to Macrolides and a New Benzoxazinorifamycin, KRM-1648," *Infectious Disease and Therapy*, 21:317-321 (1997).

Lenaerts et al., "Evaluation of Rifalazil in a Combination Treatment Regimen as an Alternative to Isoniazid-Rifampin Therapy in a Mouse Tuberculosis Model," *Antimicrobial Agents and Chemotherapy* 44(11):3167-3168 (2000).

Mae et al., "Effect of a New Rifamycin Derivative, Rifalazil, on Liver Microsomal Enzyme Induction in Rat and Dog," *Xenobiotica* 28(8):759-766 (1998).

Mae et al., "Isolation and Identification of Major Metabolites of Rifalazil in Mouse and Human," *Xenobiotica* 29:1073-1087 (1999).

Roblin et al., "In Vitro Activities of Rifamycin Derivatives ABI-1648 (Rifalazil, KRM-1648), ABI-1657, and ABI-1131 Against Chlamydia Trachomatis and Recent Clinical Isolates of Chlamydia Pneumoniae," *Antimicrobial Agents and Chemotherapy* 47:1135-1136 (2003).

Saito et al., "Therapeutic Efficacy of Benzoxazinorifamycin, KRM-1648, Against Disseminated *Mycobacterium avium* Infection Induced in Rabbits," *Abstracts of the General Meeting of the American Society for Microbiology* 93:174 (1993). [*Abstract U31*].

Sano et al., "Therapeutic Effects of Benzoxazinorifamycin KRM-1648 Administered Alone or in Combination with a Half-sized Secretory Leukocyte Protease Inhibitor or the Nonsteroidal Anti-inflammatory Drug Diclofenac Sodium against *Mycobacterium avium* Complex Infection in Mice," *Antimicrobial Agents and Chemotherapy* 43(2):360-364 (1999).

Sato et al., "Antimicrobial Activities of Benzoxazinorifamycin KRM-1648, Clarithromycin and Levofloxacin Against Intracellular *Mycobacterium avium* Complex Phagocytosed by Murine Peritoneal Macrophages," *Journal of Antimicrobial Chemotherapy* 41(1):77-83 (1998).

Seligson et al., "A New Prodrug of Paclitaxel: Synthesis of Protaxel." *Anti-Cancer Drugs* 12(4):305-313 (2001).

Shimizu et al., "Effects of the Chinese Traditional Medicine Maobushi-saishin-to on Therapeutic Efficacy of a New Benzoxazinorifamycin, KRM-1648, Against *Mycobacterium avium* Infection in Mice," *Antimicrobial Agents and Chemotherapy* 43(3):514-519 (1999).

Shoen et al., "Evaluation of Rifalazil in Long-term Treatment Regimens for Tuberculosis in Mice," *Antimicrobial Agents and Chemotherapy* 44(6):1458-1462 (2000).

Tomioka et al., "Effects of Benzoxazinorifamycin KRM-1648 on Cytokine Production at Sites of *Mycobacterium avium* Complex Infection Induced in Mice," *Antimicrobial Agents and Chemotherapy* 41(2):357-362 (1997).

Tomioka et al., "In Vivo Antileprosy Activity of the Newly Synthesized Benzoxazinorifamycin, KRM-1648," *International Journal of Leprosy* 61(2):255-258 (1993).

Tomioka et al., "Intramacrophage Passage of Mycobacterium Tuberculosis and *M. avium* Complex Alters the Drug Susceptibilities of the Organisms as Determined by Intracellular Susceptibility Testing using Macrophages and Type II Alveolar Epithelial Cells," *Antimicrobial Agents and Chemotherapy* 46(2):519-521 (2002).

Tomioka et al., "Therapeutic Efficacy of KRM-1648 in Combination with Other Antimicrobials Against *M. leprae* Infection Induced in Nude Mice," *International Journal of Leprosy and Other Mycobacterial Diseases* 61:77A (1993). [*Abstract EX9*].

Wallis et al., "Inhibition of Isoniazid-induced Expression of Mycobacterium Tuberculosis Antigen 85 in Sputum: Potential Surrogate Marker in Tuberculosis Chemotherapy Trials," *Antimicrobial Agents and Chemotherapy* 45(4):1302-1304 (2001).

Yamamoto et al., "Activity of KRM-1648 Alone or in Combination with Both Ethambutol and Kanamycin or Clarithromycin Against Mycobacterium Intracellulare Infections in Beige Mice," *Antimicrobial Agents and Chemotherapy* 40(2):429-432 (1996).

Yamamoto et al., "In Vitro Bactericidal and In Vivo Therapeutic Activities of a New Rifamycin Derivative, KRM-1648, Against Mycobacterium Tuberculosis," *Antimicrobial Agents and Chemotherapy* 40(2):426-428 (1996).

Yamane T. et al., "Synthesis and Biological Activity of 3'-hydroxy-5'-Aminobenzoxazinorifamycin Derivatives." *Chemical and Pharmaceutical Bulletin* 41(1):148-155 (1993).

RIFAMYCIN ANALOGS AND USES THEREOF

CROSS-REFERENCE TO RELATED APPLICATIONS

This application is a continuation application of Ser. No. 11/008,597, filed Dec. 9, 2004, which claims priority from U.S. Provisional Application Ser. No. 60/528,733, filed Dec. 10, 2003, each of which is hereby incorporated by reference.

BACKGROUND OF THE INVENTION

The present invention relates to the field of antimicrobial agents.

The use of antibiotics by humans can be seen as an evolutionary experiment of enormous magnitude, a window from which to view not-quite-natural selection operating in real time. Within 50 years, the number of species and strains of pathogenic and commensal bacteria resistant to antibiotics and the number of antibiotics to which they are resistant has increased virtually monotonically world-wide. As a result, infections that had been readily treatable by chemotherapy may no longer be so. It is clear that the evolution and spread of resistance can be attributed to the use and overuse of antibiotics. Increased resistance of bacterial infections to antibiotic treatment has been extensively documented and has now become a generally recognized medical problem, particularly with nosocomial infections. See, for example, Jones et al., *Diagn. Microbiol. Infect. Dis.* 31:379-388, 1998; Murray, *Adv. Intern. Med.* 42:339-367, 1997; and Nakae, *Microbiologia* 13:273-284, 1997.

Throughout the developed world there is public and governmental concern about the increasing prevalence of antimicrobial resistance to chemotherapy in bacteria that cause diseases in humans. Many pathogens exist for which there are few effective treatments, and the number of strains resistant to available drugs is continually increasing. New antimicrobial agents and improved methods are thus needed for the treatment and prevention of infections by such pathogens.

SUMMARY OF THE INVENTION

The present invention features rifamycin analogs that can be used as therapeutics for treating or preventing a variety of microbial infections.

Accordingly in a first aspect, the invention features a compound having the formula:

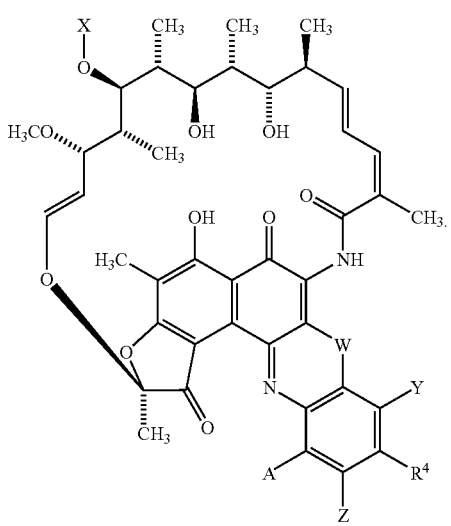

(I)

In formula I, A is H, OH, O—($C_1$-$C_6$ alkyl), O—($C_1$-$C_4$ alkaryl), O—($C_6$-$C_{12}$ aryl), O—($C_1$-$C_9$ heteroaryl), or O—($C_1$-$C_4$ alkheteroaryl). Preferably A is H, OH, O—($C_1$-$C_6$ alkyl), or O—($C_1$-$C_4$ alkaryl).

W is O, S, or $NR^1$, where $R^1$ is H, $C_1$-$C_6$ alkyl, $C_1$-$C_4$ alkaryl, or $C_1$-$C_4$ alkheteroaryl. Preferably $R^1$ is H or $C_1$-$C_6$ alkyl.

X is H or $COR^2$, where $R^2$ is $C_1$-$C_6$ alkyl, which can be substituted with from 1 to 5 OH groups, or O—($C_3$-$C_7$ alkyl), which can be substituted with from 1 to 4 OH groups, with each carbon atom of the alkyl group bonded to no more than one oxygen. $R^2$ can also represent $C_6$-$C_{12}$ aryl, $C_1$-$C_4$ alkaryl, $C_1$-$C_9$ heteroaryl, or $C_1$-$C_4$ alkheteroaryl.

$R^4$ is $OR^5$, $SR^5$, or $NR^5R^6$, where $R^5$ and $R^7$, which is a substituent on Z as described below, together represent a bond or form a substituted or unsubstituted $C_1$-$C_4$ linkage (i.e., the $R^4$ and Z substituents form a ring) and $R^6$ is H, $C_1$-$C_6$ alkyl, $C_1$-$C_6$ alkaryl, $COR^9$, $CO_2R^9$, $CONHR^9$, $CSR^9$, $COSR^9$, $CSOR^9$, $CSNHR^9$, $SO_2R^9$, or $SO_2NHR^9$, where $R^9$ is $C_1$-$C_6$ alkyl, $C_6$-$C_{12}$ aryl, $C_1$-$C_4$ alkaryl, heteroaryl, or $C_1$-$C_4$ alkheteroaryl. $R^6$ can also represent $C_6$-$C_{12}$ aryl, $C_1$-$C_9$ heteroaryl, or $C_1$-$C_4$ alkheteroaryl.

Y is H, Hal, or $OR^3$, where $R^3$ is $C_1$-$C_6$ alkyl, $C_6$-$C_{12}$ aryl, $C_1$-$C_4$ alkaryl, $C_1$-$C_9$ heteroaryl, or $C_1$-$C_4$ alkheteroaryl. Preferably, $R^3$ is $C_1$-$C_6$ alkyl or $C_1$-$C_4$ alkaryl.

Z is $(CR^{11}R^{12})_nNR^7R^8$, where n is 0 or 1, $R^8$ is H, $C_1$-$C_6$ alkyl, $C_1$-$C_4$ alkaryl, $COR^{10}$, $CO_2R^{10}$, $CONHR^{10}$, $CSR^{10}$, $COSR^{10}$, $CSOR^{10}$, $CSNHR^{10}$, $SO_2R^{10}$, or $SO_2NHR^{10}$, where $R^{10}$ is $C_1$-$C_6$ alkyl, $C_6$-$C_{12}$ aryl, $C_1$-$C_4$ alkaryl, heteroaryl, or $C_1$-$C_4$ alkheteroaryl. $R^8$ can also represent $C_6$-$C_{12}$ aryl, $C_1$-$C_9$ heteroaryl, or $C_1$-$C_4$ alkheteroaryl, or $R^8$ does not exist and a double bond is formed between N and an $R^5$-$R^7$ $C_1$ carbon linkage. Each of $R^{11}$ and $R^{12}$ is, independently, H, $C_1$-$C_6$ alkyl, $C_1$-$C_4$ alkaryl, or $C_1$-$C_4$ alkheteroaryl, or $R^{12}$ does not exist and a double bond is formed between N and the carbon bearing $R^{11}$.

Alternatively, for a compound of formula I, each of A, W, X is, respectively, as defined above; Z is H, Hal, or $OR^3$, where $R^3$ is as previously defined; $R^4$ is $OR^5$, $SR^5$, or $NR^5R^6$, where $R^6$ is as previously defined and $R^5$, together with $R^7$, which is a substituent on Y as described below, represent a bond or form a substituted or unsubstituted $C_1$-$C_4$ linkage (i.e., the $R^4$ and Y substituents form a ring); and Y is $(CR^{11}R^{12})_nNR^7R^8$, where each of n and $R^8$ is as previously defined.

In one embodiment, W is O, S, or $NR^1$, where $R^1$ is H or $C_1$-$C_6$ alkyl. In another embodiment, X can be either H or $COR^2$, where $R^2$ is $C_1$-$C_6$ alkyl, which can be substituted with from 1 to 5 OH groups, or O—($C_3$-$C_7$ alkyl), which can be substituted with from 1 to 4 OH groups, with each carbon atom of the alkyl group bonded to no more than one oxygen. In yet another embodiment, A is OH.

The invention also features a pharmaceutical composition that includes a compound of formula I and a pharmaceutically acceptable carrier or diluent. Such pharmaceutical compositions may be formulated for oral, topical, intravenous, intramuscular, or subcutaneous administration.

In another aspect, the invention features a method of killing, treating, or preventing a microbial infection in an animal, preferably a mammal, and most preferably a human, that includes administering to the animal a compound or pharmaceutical composition of the invention. The invention further features treating or preventing diseases associated with such microbial infections. Such methods of treatment or prevention may include the oral, topical, intravenous, intramuscular, or subcutaneous administration of a composition of the invention.

The invention also features a method for treating or preventing the development of an atherosclerosis-associated disease in a patient by administering to the patient a compound of formula I in an amount effective to treat or prevent the development of the atherosclerosis-associated disease in the patient. The patient is typically diagnosed as having the atherosclerosis-associated disease (or being at increased risk of developing the disease) or as having macrophages or foam cells infected with *C. pneumoniae* prior to the administration of a compound of formula I.

The invention also features a method of reducing the level of C-reactive protein in a patient in need thereof by administering to the patient a compound of formula I in an amount effective to reduce the level of C-reactive protein in the patient. In one embodiment, the patient has not been diagnosed as having a bacterial infection. In another embodiment, the patient has been diagnosed as having macrophages or foam cells infected with *C. pneumoniae*.

The invention also features a method for reducing *C. pneumoniae* replication in macrophages or foam cells in a patient in need thereof by administering a compound of formula I to the patient in an amount effective to reduce *C. pneumoniae* replication in macrophages or foam cells in the patient.

The invention also features a method for treating a persistent *C. pneumoniae* infection in macrophages or foam cells in a patient by administering a compound of formula I to the patient in an amount effective to treat the *C. pneumoniae* infection in macrophages or foam cells in the patient.

The invention also features a method for treating a chronic disease associated with an infection of *C. pneumoniae* by administering a compound of formula I to the patient in an amount effective to treat the infection.

In any of the foregoing aspects, the dosage of a compound of formula I is normally about 0.001 to 1000 mg/day. The compound may be given daily (e.g., a single oral dose of 2.5 to 25 mg/day) or less frequently (e.g., a single oral dose of 5, 12.5, or 25 mg/week). Treatment may be for one day to one year, or longer. In one embodiment, a compound of formula I is administered at an initial dose of 2.5 to 100 mg for one to seven consecutive days, followed by a maintenance dose of 0.005 to 10 mg once every one to seven days for one month, one year, or even for the life of the patient.

If desired, a compound of formula I may be administered in conjunction with one or more additional agents such as anti-inflammatory agents (e.g., non-steroidal anti-inflammatory drugs (NSAIDs; e.g., detoprofen, diclofenac, diflunisal, etodolac, fenoprofen, flurbiprofen, ibuprofen, indomethacin, ketoprofen, meclofenameate, mefenamic acid, meloxicam, nabumeone, naproxen sodium, oxaprozin, piroxicam, sulindac, tolmetin, celecoxib, rofecoxib, aspirin, choline salicylate, salsalte, or sodium or magnesium salicylate) or steroids (e.g., cortisone, dexamethasone, hydrocortisone, methylprednisolone, prednisolone, prednisone, or triamcinolone)), antibacterial agents (e.g., azithromycin, clarithromycin, erythromycin, gatifloxacin, levofloxacin, amoxicillin, metronidazole, penicillin G, penicillin V, methicillin, oxacillin, cloxacillin, dicloxacillin, nafcillin, ampicillin, carbenicillin, ticarcillin, mezlocillin, piperacillin, azlocillin, temocillin, cepalothin, cephapirin, cephradine, cephaloridine, cefazolin, cefamandole, cefuroxime, cephalexin, cefprozil, cefaclor, loracarbef, cefoxitin, cefmatozole, cefotaxime, ceftizoxime, ceftriaxone, cefoperazone, ceftazidime, cefixime, cefpodoxime, ceftibuten, cefdinir, cefpirome, cefepime, BAL5788, BAL9141, imipenem, ertapenem, meropenem, astreonam, clavulanate, sulbactam, tazobactam, streptomycin, neomycin, kanamycin, paromycin, gentamicin, tobramycin, amikacin, netilmicin, spectinomycin, sisomicin, dibekalin, isepamicin, tetracycline, chlortetracycline, demeclocycline, minocycline, oxytetracycline, methacycline, doxycycline, telithromycin, ABT-773, lincomycin, clindamycin, vancomycin, oritavancin, dalbavancin, teicoplanin, quinupristin and dalfopristin, sulphanilamide, para-aminobenzoic acid, sulfadiazine, sulfisoxazole, sulfamethoxazole, sulfathalidine, linezolid, nalidixic acid, oxolinic acid, norfloxacin, perfloxacin, enoxacin, ofloxacin, ciprofloxacin, temafloxacin, lomefloxacin, fleroxacin, grepafloxacin, sparfloxacin, trovafloxacin, clinafloxacin, moxifloxacin, gemifloxacin, sitafloxacin, daptomycin, garenoxacin, ramoplanin, faropenem, polymyxin, tigecycline, AZD2563, or trimethoprim), platelet aggregation inhibitors (e.g., abciximab, aspirin, cilostazol, clopidogrel, dipyridamole, eptifibatide, ticlopidine, or tirofiban), anticoagulants (e.g., dalteparin, danaparoid, enoxaparin, heparin, tinzaparin, or warfarin), antipyretics (e.g., acetaminophen), or lipid lowering agents (e.g., cholestyramine, colestipol, nicotinic acid, gemfibrozil, probucol, ezetimibe, or statins such as atorvastatin, rosuvastatin, lovastatin simvastatin, pravastatin, cerivastatin, or fluvastatin). These additional agents may be administered within 14 days, 7 days, 1 day, 12 hours, or 1 hour of administration of a compound of formula I, or simultaneously therewith. The additional therapeutic agents may be present in the same or different pharmaceutical compositions as the compound of formula I. When present in different pharmaceutical compositions, different routes of administration may optionally be used. For example, a compound of formula I may be administered orally, while a second agent may be administered by intravenous, intramuscular, or subcutaneous injection.

The invention also features a stent coated with a compound of formula I. The stent can be, e.g., a wire mesh tube used to hold open an artery. Stents are typically inserted following angioplasty.

The invention also features methods and compositions for treating or preventing an ear infection in a patient by orally administering or topically administering to the affected otic area (e.g., the tympanic membrane or the external auditory canal of the ear) of the patient a pharmaceutical composition including a therapeutically effective amount of a compound of formula I. The compositions and methods of the invention can also be used to treat or prevent infections that result from surgery.

The invention also features a pharmaceutical composition suitable for topical administration to the ear of a patient containing a compound of formula I and a pharmaceutically-acceptable excipient, administered at a dose capable of reducing the infection in the patient. According to this invention, the compound of formula I can be in the amount between 0.001% and 5% weight/volume (w/v), preferably 0.01% and 3% w/v, more preferably 0.1% and 1% w/v, or most preferably 0.1% and 0.4% w/v. The compound of formula I can also be impregnated in a porous media (for example, an ear wick such as a sponge, gauze, cotton, or hydrocellulose), which is suitable for insertion into the ear of a patient. If desired, the composition may also include one or more penetration enhancers (e.g., alcohols, polyols, sulfoxides, esters, ketones, amides, oleates, surfactants, alkanoic acids, lactam compounds, alkanols, or admixtures thereof).

In another aspect, the invention also features a method for treating or preventing the development of an ear infection in a patient using a composition described above. A compound of formula I can be administered to the infected ear by means of drops or by the insertion of a compound-impregnated porous media into the external ear canal to the tympanic membrane. Ear infections that can be treated using the methods and composition of the invention include otitis media and otitis externa. Types of otitis media amenable to treatment include, for example, acute otitis media, otitis media with effusion, and chronic otitis media. Types of otitis externa include acute otitis externa, chronic otitis externa, and malignant otitis externa.

A compound of the invention can also be administered to the ear (e.g., the tympanic membrane or the external auditory canal of the ear) to treat or prevent bacterial infections associated with otitis media (e.g., an infection of *H. influenza, M. catarhalis,* or *S. pneumoniae*) or otitis externa (e.g., an infection of *S. intermedius, Streptococcus* spp. *Pseudomonas* spp., *Proteus* spp., or *E. coli*).

The methods and compositions of the invention are also useful to treat infections associated with otic surgical procedures such as tympanoplasty, stapedectomy, removal of tumors, or cochlear implant surgery. The compositions may also be used prophylactically, prior to therapies or conditions that can cause ear infections. Compositions containing a compound of formula I can therefore be applied to an area of the ear to which the surgical intervention will be performed, within at least seven days (before or after) of the surgical intervention. When treating a patient affected with otitis externa, an acidification therapy involving the administration of an acetic acid solution to the ear of the patient may also be performed.

Typically, patients are administered one to four drops of a compound of the invention in a total amount between 0.001% and 5% w/v, preferably 0.01% and 3% w/v, more preferably 0.1% and 1% w/v, or most preferably 0.1% and 0.4% w/v. The composition may be given daily (e.g., once, twice, three times, or four times daily) or less frequently (e.g., once every other day, or once or twice weekly). Treatment may be for 1 to 21 days, desirably 1 to 14 days, or even 3 to 7 days. Additional therapeutic agents, such as anti-inflammatory agents (e.g., non-steroidal anti-inflammatory or steroid), anesthetics, zinc salts, or other antimicrobial agents, can also be administered with a compound of the invention. Non-steroidal anti-inflammatory agents include, for example, detoprofen, diclofenac, diflunisal, etodolac, fenoprofen, flurbiprofen, indomethacin, ketoprofen, mechlofenameate, mefenamic acid, meloxicam, nabumeone, naproxen sodium, oxaprozin, piroxicam, sulindac, tolmeting, celecoxib, rofecoxib, choline salicylate, salsate, sodium salicylate, magnesium salicylate, aspirin, ibuprofen, paracetamol, acetaminophen, and pseudoephedrine and steroids include, for example, hydrocortisone, prednisone, fluprednisolone, triamcinolone, dexamethasone, betamethasone, cortisone, prednilosone, methylprednisolone, fluocinolone acetonide, flurandrenolone acetonide, and fluorometholone. Anesthetics according to the invention can be, for example, benzocaine, butamben picrate, tetracaine, dibucaine, prilocalne, etidocaine, mepivacaine, bupivicaine, and lidocaine. A zinc salt can be zinc sulfate, zinc chloride, zinc acetate, zinc phenol sulfonate, zinc borate, zinc bromide, zinc nitrate, zinc glycerophosphate, zinc benzoate, zinc carbonate, zinc citrate, zinc hexafluorosilicate, zinc diacetate trihydrate, zinc oxide, zinc peroxide, zinc salicylate, zinc silicate, zinc stannate, zinc tannate, zinc titanate, zinc tetrafluoroborate, zinc gluconate, and zinc glycinate, and antimicrobial agents according to the invention include, for example, azithromycin, clarithromycin, erythromycin, gatifloxacin, levofloxacin, amoxicillin, metronidazole, penicillin G, penicillin V, methicillin, oxacillin, cloxacillin, dicloxacillin, nafcillin, ampicillin, carbenicillin, ticarcillin, mezlocillin, piperacillin, azlocillin, temocillin, cepalothin, cephapirin, cephradine, cephaloridine, cefazolin, cefamandole, cefuroxime, cephalexin, cefprozil, cefaclor, loracarbef, cefoxitin, cefmatozole, cefotaxime, ceftizoxime, ceftriaxone, cefoperazone, ceftazidime, cefixime, cefpodoxime, ceftibuten, cefdinir, cefpirome, cefepime, BAL5788, BAL9141, imipenem, ertapenem, meropenem, astreonam, clavulanate, sulbactam, tazobactam, streptomycin, neomycin, kanamycin, paromycin, gentamicin, tobramycin, amikacin, netilmicin, spectinomycin, sisomicin, dibekalin, isepamicin, tetracycline, chlortetracycline, demeclocycline, minocycline, oxytetracycline, methacycline, doxycycline, telithromycin, ABT-773, lincomycin, clindamycin, vancomycin, oritavancin, dalbavancin, teicoplanin, quinupristin and dalfopristin, sulphanilamide, para-aminobenzoic acid, sulfadiazine, sulfisoxazole, sulfamethoxazole, sulfathalidine, linezolid, nalidixic acid, oxolinic acid, norfloxacin, perfloxacin, enoxacin, ofloxacin, ciprofloxacin, temafloxacin, lomefloxacin, fleroxacin, grepafloxacin, sparfloxacin, trovafloxacin, clinafloxacin, moxifloxacin, gemifloxacin, sitafloxacin, daptomycin, garenoxacin, ramoplanin, faropenem, polymyxin, tigecycline, AZD2563, or trimethoprim. These additional therapeutic agents can be present in the same or different pharmaceutical compositions as a compound of formula I. When a therapeutic agent is present in a different pharmaceutical composition, different routes of administration may be used. A compound of formula I and the second therapeutic agent, for example, may also be administered within 24 hours of each other, and an anti-inflammatory agent, for example, may be administered orally, or by intravenous, intramuscular, or subcutaneous injection.

To increase the efficacy of a topically administered composition containing a compound of the invention, it is desirable that the amount of debris and granulation tissue are reduced at least once a day in the infected ear of the patient and at least one hour prior to the administration of a compound of the invention. Debris can be removed, for example, by suction, irrigation with a solution containing hydrogen peroxide, cauterization, or by manual techniques employing microinstruments and microscope. Reduction in the amount of granulation tissue in the infected ear may be performed by means of cauterizing, or by the administration of a steroid.

The invention also features a pharmaceutical pack containing (i) a compound of formula I in an amount effective to treat a patient having an ear infection; and (ii) instructions for administering the compound to the ear of a patient. The invention also features a composition containing a compound of formula I and a pharmaceutical excipient suitable for topical administration to the ear. If desired, an applicator for applying the composition to the ear may also be included. Desirably, the composition contains a compound of formula I in the amount between 0.001% and 5% weight/volume (w/v), preferably 0.01% and 3% w/v, more preferably 0.1% and 1% w/v, or most preferably 0.1% and 0.4% w/v and is present in amounts sufficient to treat for at least 1, 3, 5, 7, 10, 14, or 21 days. A penetration enhancer may also be added (e.g., alcohols, polyols, sulfoxides, esters, ketones, amides, oleates, surfactants, alkanoic acids, lactam compounds, alkanols, or admixtures thereof).

The invention also features a method for treating chronic gastritis, gastric ulcer, or duodenal ulcer associated with an infection of *H. pylori*, or preventing the disease or infection, in a patient. The method includes the step of administering, preferably, orally administering, to the patient an effective amount of a compound of formula I to treat the patient. The compound is normally administered at about 0.1 to 1000 mg/day (desirably about 1 to 100 mg/day, more desirably about 1 to 50 mg/day, and even more desirably about 1 to 25 mg/day). The compound may be given daily (e.g., once, twice, three times, or four times daily) or less frequently (e.g., once every other day, or once or twice weekly). Treatment may be for 1 to 21 days, desirably 1 to 14 days or even 3 to 7 days. If desirable, a compound of the invention can be administered with a proton pump inhibitor (e.g., omeprazole, esomeprazole, lansoprazole, leminoprazole, pantoprazole, or robeprazole), and/or bismuth preparation (e.g., colloidal bismuth subcitrate or bismuth subsalicylate).

The invention also features a pharmaceutical pack including (i) a compound of formula I in an amount effective to treat chronic gastritis, gastric ulcer, or duodenal ulcer associated with an infection of *H. pylori* in a patient; and (ii) instructions for administering the compound to the patient. Desirably, the compound is in unit amounts of between 0.1 and 1000 mg (e.g., between 1 and 50 mg or between 5 and 50 mg), and is present in amounts sufficient to treat for at least 1, 3, 5, 7, 10, 14, or 21 days. The pack may optionally include a proton pump inhibitor and/or bismuth preparation. In one embodiment, a compound of formula I is in a pharmaceutical composition with the proton pump inhibitor and/or bismuth preparation.

The invention also features a method for treating a patient having antibiotic-associated bacterial diarrhea or an infection of *C. difficile*, or preventing the disease or infection in the patient. The method includes the step of orally administering to the patient an effective amount of a compound of formula I to treat the patient. The compound is normally administered at about 0.1 to 1000 mg/day (desirably about 1 to 100 mg/day, more desirably about 1 to 50 mg/day, and even more desirably about 1 to 25 mg/day). The compound may be given daily (e.g., once, twice, three times, or four times daily) or less frequently (e.g., once every other day, or once or twice weekly). Treatment may be for 1 to 21 days, desirably 1 to 14 days or even 3 to 7 days. In one embodiment, a compound of the invention is administered at an initial dose of between 5 and 100 mg, followed by subsequent doses of between 1 and 50 mg for 3 to 7 days. A single dose (e.g., in a dosage of between 5 and 50 mg) can also be employed in the method of the invention. If desirable, a compound of formula I can be administered with a second antibiotic (e.g., metronidazole or vancomycin), either simultaneously or sequentially.

The invention also features a pharmaceutical pack including (i) a compound of formula I in an amount effective to treat a patient having antibiotic-associated bacterial diarrhea or an infection of *C. difficile*; and (ii) instructions for administering the compound to the patient for treating or preventing a *C. difficile* infection. Desirably, the compound is in unit amounts of between 1 and 1000 mg (e.g., between 1 and 50 mg or between 5 and 50 mg), and is present in amounts sufficient to treat for at least 1, 3, 5, 7, 10, 14, or 21 days.

The invention features a method for treating a patient having an infection of *Chlamydia trachomatis*. The method includes the step of administering to the patient a compound of formula I in an amount effective to treat the patient. In one embodiment, the patient is administered the compound as a single oral dose.

The invention also features a pharmaceutical pack that includes (i) a single oral dose of a compound of formula I in an amount effective to treat a patient having an infection of *C. trachomatis* or *N. gonorrhoeae*; and (ii) instructions for administering the single oral dose to the patient. Desirably, the dose is in an amount between 0.1 and 100 mg (e.g., between 1 and 50 mg or between 5 and 25 mg).

The invention also features a method of treating a patient having a chronic disease associated with a bacterial infection caused by bacteria capable of establishing a cryptic phase. This method includes the step of administering to a patient a compound of formula I for a time and in an amount sufficient to treat the cryptic phase of the bacterial infection. The chronic disease may be an inflammatory disease. Examples of inflammatory diseases include, but are not limited to, asthma, coronary artery disease, arthritis, conjunctivitis, lymphogranuloma venerum (LGV), cervicitis, and salpingitis.

The chronic disease can also be an autoimmune disease (e.g., systemic lupus erythematosus, diabetes mellitus, or graft versus host disease).

The invention also features a method for treating a patient diagnosed as being infected with a bacterium having a multiplying form and a non-multiplying form by administering to the patient (i) a compound of formula I and (ii) a second antibiotic that is effective against the multiplying form of the bacterium, wherein the two antibiotics are administered in amounts and for a duration that, in combination, effectively treat the patient. In a related aspect, the invention features a method of treating a patient with a chronic disease associated with a persistent bacterial infection by administering a compound of formula I.

In preferred embodiments of any of the foregoing aspects, the persistent intracellular bacterial infection is caused by one of the following: *Chlamydia* spp. (e.g., *C. trachomatis, C. pneumoniae, C. psittaci, C. suis, C. pecorum, C. abortus, C. caviae, C. felis, C. muridarum*), *N. hartmannellae, W. chondrophila, S. negevensis*, or *P. acanthamoeba*.

The time sufficient to treat a bacterial infection ranges from one week to one year, but it can also be extended over the lifetime of the individual patient, if necessary. In more preferable embodiments, the duration of treatment is at least 30 days, at least 45 days, at least 100 days, or at least 180 days. Ultimately, it is most desirable to extend the treatment for such a time that the bacterial infection is no longer detected.

Compounds of formula I are useful against drug resistant Gram-positive cocci, such as methicillin-resistant *S. aureus* and vancomycin-resistant enterococci, and are useful in the treatment of community-acquired pneumonia, upper and lower respiratory tract infections, skin and soft tissue infections, hospital-acquired lung infections, bone and joint infections, and other bacterial infections.

The compounds and methods of the present invention can be used to treat, for example, respiratory tract infections, acute bacterial otitis media, bacterial pneumonia, urinary tract infections, complicated infections, noncomplicated infections, pyelonephritis, intra-abdominal infections, deep-seated abcesses, bacterial sepsis, skin and skin structure infections, soft tissue infections, bone and joint infections, central nervous system infections, bacteremia, wound infections, peritonitis, meningitis, infections after burn, urogenital tract infections, gastro-intestinal tract infections, pelvic inflammatory disease, endocarditis, and other intravascular infections.

The compounds and methods of the present invention can also be used to treat diseases associated with bacterial infection. For example, bacterial infections can produce inflammation, resulting in the pathogenesis of atherosclerosis, multiple sclerosis, rheumatoid arthritis, diabetes, Alzheimer's disease, asthma, cirrhosis of the liver, psoriasis, meningitis, cystic fibrosis, cancer, or osteoporosis. Accordingly, the present invention also features a method of treating the diseases associated with bacterial infection listed above.

The methods of the present invention can be used to treat or prevent infections by bacteria from a variety of genera, such as *Escherichia* spp., *Enterobacter* spp., *Enterobacteriaceae* spp., *Klebsiella* spp., *Serratia* spp., *Pseudomonas* spp., *Acinetobacter* spp., *Bacillus* spp., *Micrococcus* spp., *Arthrobacter* spp., *Peptostreptococcus* spp., *Staphylococcus* spp., *Enterococcus* spp., *Streptococcus* spp., *Haemophilus* spp., *Neisseria* spp., *Bacteroides* spp., *Citrobacter* spp., *Branhamella* spp., *Salmonella* spp., *Shigella* spp., *Proteus* spp., *Clostridium* spp., *Erysipelothrix* spp., *Listeria* spp., *Pasteurella* spp., *Streptobacillus* spp., *Spirillum* spp., *Fusospirocheta* spp., *Treponema* spp., *Borrelia* spp., *Actinomycetes* spp., *Mycoplasma* spp., *Chlamydia* spp., *Rickettsia* spp., *Spirochaeta* spp., *Legionella* spp., *Mycobacteria* spp., *Ureaplasma* spp., *Streptomyces* spp., and *Trichomoras* spp. Accordingly, the invention features a method of treating infections by the bacteria belonging to the genera above, among others.

Particular Gram-positive bacterial infections that can be treated according to the methods of the invention include infections by *Staphylococcus aureus*, *Staphylococcus epidermidis*, *Enterococcus faecalis*, *Enterococcus faecium*, *Clostridium perfringens*, *Streptococcus pyogenes*, *Streptococcus pneumoniae*, other *Streptococcus* spp., and other *Clostridium* spp.

Multi-drug resistant strains of bacteria can be treated according to the methods of the invention. Resistant strains of bacteria include penicillin-resistant, methicillin-resistant, quinolone-resistant, macrolide-resistant, and/or vancomycin-resistant bacterial strains. The multi-drug resistant bacterial infections to be treated using the methods of the present invention include infections by penicillin-, methicillin-, macrolide-, vancomycin-, and/or quinolone-resistant *Streptococcus pneumoniae*; penicillin-, methicillin-, macrolide-, vancomycin-, and/or quinolone-resistant *Staphylococcus aureus*; penicillin-, methicillin-, macrolide-, vancomycin-, and/or quinolone-resistant *Streptococcus pyogenes*; and penicillin-, methicillin-, macrolide-, vancomycin-, and/or quinolone-resistant enterococci.

The invention also features a method of eradicating non-multiplying bacteria that are not eradicated in a patient following treatment with a first antibiotic by administering to the patient a compound of formula I in an amount and for a duration sufficient to eradicate the non-multiplying bacteria in the patient.

Compounds of the invention may also be used to treat or prevent viral infections.

In another aspect, the invention features a pharmaceutical composition that includes a compound described herein in any pharmaceutically acceptable form, including isomers such as diastereomers and enantiomers, salts, solvates, and polymorphs thereof. In various embodiments, the composition includes a compound of the invention along with a pharmaceutically acceptable carrier or diluent.

In another aspect, the invention features a method of treating a microbial infection in an animal comprising co-administering a compound of the invention along with one or more antifungal agents, antiviral agents, antibacterial agents, or antiprotozoan agents, or combinations thereof.

In any of the above aspects, desirable compounds include the following compounds of formula I:

(a) the compound where A is OH, X is COCH$_3$, W is O, Z is H, and, together, Y and R$^4$ are

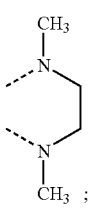

(b) the compound where A is OH, X is H, W is O, Z is H, and, together, Y and R$^4$ are

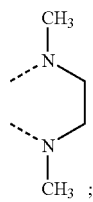

(c) the compound where A is OH, X is COCH$_3$, W is O, Z is H, and, together, Y and R$^4$ are

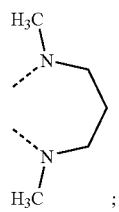

(d) the compound where A is OH, X is H, W is O, Z is H, and, together, Y and R$^4$ are

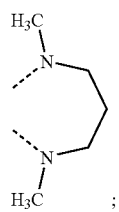

(e) the compound where A is OH, X is COCH$_3$, W is O, Z is H, and, together, Y and R$^4$ are

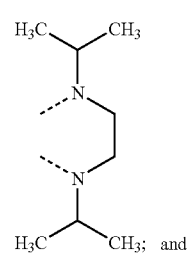

and (f) the compound where A is OH, X is COCH$_3$, W is O, Z is H, and, together, Y and R$^4$ are

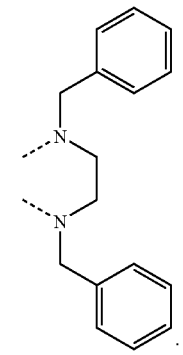

As used herein, the terms "alkyl" and the prefix "alk-" are inclusive of both straight chain and branched chain saturated or unsaturated groups, and of cyclic groups, i.e., cycloalkyl and cycloalkenyl groups. Unless otherwise specified, acyclic alkyl groups are from 1 to 6 carbons. Cyclic groups can be monocyclic or polycyclic and preferably have from 3 to 8 ring carbon atoms.

Exemplary cyclic groups include cyclopropyl, cyclopentyl, cyclohexyl, and adamantyl groups. Alkyl groups may be substituted with one or more substituents or unsubstituted. Exemplary substituents include alkoxy, aryloxy, sulfhydryl, alkylthio, arylthio, halogen, alkylsilyl, hydroxyl, fluoroalkyl, perfluoroalkyl, amino, aminoalkyl, disubstituted amino, quaternary amino, hydroxyalkyl, carboxyalkyl, and carboxyl groups.

By "aryl" is meant a carbocyclic aromatic ring or ring system. Unless otherwise specified, aryl groups are from 6 to 18 carbons. Examples of aryl groups include phenyl, naphthyl, biphenyl, fluorenyl, and indenyl groups.

By "heteroaryl" is meant an aromatic ring or ring system that contains at least one ring hetero-atom (e.g., O, S, Se, N, or P). Unless otherwise specified, heteroaryl groups are from 1 to 9 carbons. Heteroaryl groups include furanyl, thienyl, pyrrolyl, imidazolyl, pyrazolyl, oxazolyl, isoxazolyl, thiazolyl, isothiazolyl, triazolyl, tetrazolyl, oxadiazolyl, oxatriazolyl, pyridyl, pyridazyl, pyrimidyl, pyrazyl, triazyl, benzofuranyl, isobenzofuranyl, benzothienyl, indole, indazolyl, indolizinyl, benzisoxazolyl, quinolinyl, isoquinolinyl, cinnolinyl, quinazolinyl, naphtyridinyl, phthalazinyl, phenanthrolinyl, purinyl, and carbazolyl groups.

By "heterocycle" is meant a non-aromatic ring or ring system that contains at least one ring heteroatom (e.g., O, S, Se, N, or P). Unless otherwise specified, heterocyclic groups are from 2 to 9 carbons. Heterocyclic groups include, for example, dihydropyrrolyl, tetrahydropyrrolyl, piperazinyl, pyranyl, dihydropyranyl, tetrahydropyranyl, dihydrofuranyl, tetrahydrofuranyl, dihydrothiophene, tetrahydrothiophene, and morpholinyl groups.

Aryl, heteroaryl, or heterocyclic groups may be unsubstituted or substituted by one or more substituents selected from the group consisting of C$_{1-6}$ alkyl, hydroxyl, halo, nitro, C$_{1-6}$ alkoxy, C$_{1-6}$ alkylthio, trifluoromethyl, C$_{1-6}$ acyl, arylcarbonyl, heteroarylcarbonyl, nitrile, C$_{1-6}$ alkoxycarbonyl, alkaryl (where the alkyl group has from 1 to 4 carbon atoms) and alkheteroaryl (where the alkyl group has from 1 to 4 carbon atoms).

By "alkoxy" is meant a chemical substituent of the formula —OR, where R is an alkyl group. By "aryloxy" is meant a chemical substituent of the formula —OR', where R' is an aryl group. By "alkaryl" is meant a chemical substituent of the formula —RR', where R is an alkyl group and R' is an aryl group, By "alkheteraryl" is meant a chemical substituent of the formula RR", where R is an alkyl group and R" is a heteroaryl group.

By "halide" or "halogen" or "halo" is meant bromine, chlorine, iodine, or fluorine.

By "non-vicinal O, S, or NR" is meant an oxygen, sulfur, or nitrogen heteroatom substituent in a linkage, where the heteroatom substituent does not form a bond to a saturated carbon that is bonded to another heteroatom.

In structural representations where the chirality of a carbon has been left unspecified, it is to be presumed by one skilled in the art that either chiral form of that stereocenter is possible.

By "benzoxazinorifamycin" is meant a compound described by formula (A):

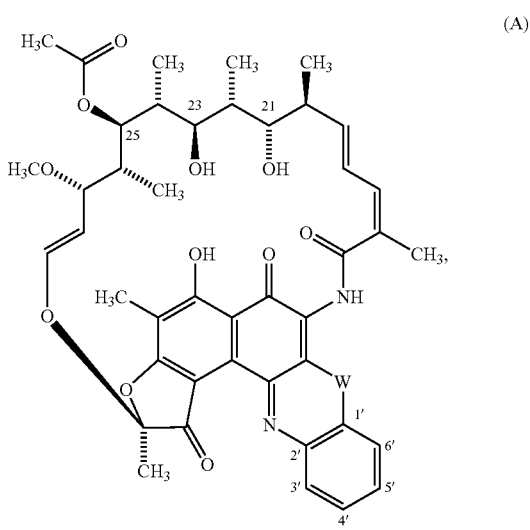

where W is O. By "benzthiazinorifamycin" is meant a compound described by formula (A), where W is S. By "benzdiazinorifamycin" is meant a compound described by formula (A), where W is N—R. For benzdiazinorifamycin, R can be, for example, H or an alkyl substituent. When R is an alkyl substituent, it is referred to as N'—R (e.g., N'-methyl) in the naming of the compound. Benzoxazinorifamycin, benzthiazinorifamycin, and benzdiazinorifamycin analogs that contain substituents are numbered according to the numbering provided in formula (A). By "25-O-deacetyl" rifamycin is meant a rifamycin analog in which the acetyl group at the 25-position has been removed. Analogs in which this position is further derivatized are referred to as a "25-O-deacetyl-25-(substituent)rifamycin", in which the nomenclature for the derivatizing group replaces "substituent" in the complete compound name. For example, a benzoxazinorifamycin analog in which the 25-acetyloxy group has been transformed to a carbonate group, with the other side of the carbonate bonded to a 2,3-dihydroxypropyl group, is referred to as a "25-O-deacetyl-25-(2",3"-dihydroxypropylcarbonoxy)-benzoxazinorifamycin."

By "atherosclerosis" is meant the progressive accumulation of smooth muscle cells, immune cells (e.g., lymphocytes, macrophages, or monocytes), lipid products (e.g., lipoproteins, or cholesterol), cellular waste products, calcium, or other substances within the inner lining of an artery, resulting in the narrowing or obstruction of the blood vessel and the development of atherosclerosis-associated diseases. Atherosclerosis is typically manifested within large and medium-sized arteries, and is often characterized by a state of chronic inflammation within the arteries.

By "atherosclerosis-associated disease" is meant any disorder that is caused by or is associated with atherosclerosis. Typically, atherosclerosis of the coronary arteries commonly causes coronary artery disease, myocardial infarction, coronary thrombosis, and angina pectoris. Atherosclerosis of the arteries supplying the central nervous system frequently provokes strokes and transient cerebral ischemia. In the peripheral circulation, atherosclerosis causes intermittent claudication and gangrene and can jeopardize limb viability. Atherosclerosis of an artery of the splanchnic circulation can cause mesenteric ischemia. Atherosclerosis can also affect the kidneys directly (e.g., renal artery stenosis).

A patient who is being treated for an atherosclerosis-associated disease is one who a medical practitioner has diagnosed as having such a disease. Diagnosis may be by any suitable means. Methods for diagnosing atherosclerosis by measuring systemic inflammatory markers are described, for example, in U.S. Pat. No. 6,040,147, hereby incorporated by reference. Diagnosis and monitoring may employ an electrocardiogram, chest X-ray, echocardiogram, cardiac catheterization, ultrasound (for the measurement of vessel wall thickness), or measurement of blood levels of CPK, CPK-MB, myoglobin, troponin, homocysteine, or C-reactive protein. A patient in whom the development of an atherosclerosis-associated disease is being prevented is one who has not received such a diagnosis. One in the art will understand that these patients may have been subjected to the same tests (electrocardiogram, chest X-ray, etc.) or may have been identified, without examination, as one at high risk due to the presence of one or more risk factors (e.g., family history, hypertension, diabetes mellitus, high cholesterol levels). Thus, prophylactic administration of a compound of the invention is considered to be preventing the development of an atherosclerosis-associated disease.

An atherosclerosis-associated disease has been treated or prevented when one or more tests of the disease (e.g., any of the those described above) indicate that the patient's condition has improved or the patient's risk reduced. In one example, a reduction in C-reactive protein to normal levels indicates that an atherosclerosis-associated disease has been treated or prevented.

An alternative means by which treatment or prevention is assessed includes determination of the presence of an infection of C. pneumoniae. Any suitable method may be employed (e.g., determination of C. pneumoniae in blood monocytes or in the atheroma itself (e.g., in macrophages or foam cells present in the fatty streak), or detection of C. pneumoniae DNA, RNA, or antibodies to C. pneumoniae in a biological sample from the patient).

By "debris" is meant the mucoid exudate or desquamated epithelium in an infected ear of a patient having an ear infection.

By "ear wick" is meant a sponge, cotton, gauze, compressed hydroxycellulose, or any other material used to increase the penetration of a compound of the invention to the infected otic area. The ear wick is typically inserted into the canal under direct vision. Its presence helps wick eardrops along the canal, hold the solution in contact with the skin of the canal, and apply pressure to the canal skin.

By "granulation tissue" is meant the highly vascularized tissue that replaces the initial fibrin clot in a wound. Vascularization is a result of an ingrowth of capillary endothelium from the surrounding vasculature. The tissue is also rich in fibroblasts and leucocytes.

"Antibiotic-associated bacterial diarrhea" means the condition wherein antibiotic therapy disturbs the balance of the microbial flora of the gut, allowing pathogenic organisms such as C. difficile to flourish. These organisms cause diarrhea. Antibiotic-associated bacterial diarrhea includes such conditions as C. difficile associated diarrhea (CDAD) and pseudomembranous colitis.

"Pseudomembranous colitis," also known as pseudomembranous enterocolitis or enteritis, means the inflammation of the mucous membrane of both small and large intestine with the formation and passage of pseudomembranous material (composed of fibrin, mucous, necrotic epithelial cells and leukocytes) in the stools.

By "autoimmune disease" is meant a disease arising from an immune reaction against self-antigens and directed against the individual's own tissues. Examples of autoimmune diseases include but are not limited to systemic lupus erythematosus, rheumatoid arthritis, myasthenia gravis, and Graves' disease.

By "bacteria" is meant a unicellular prokaryotic microorganism that usually multiplies by cell division.

By "bacterial infection" is meant the invasion of a host animal by pathogenic bacteria. For example, the infection may include the excessive growth of bacteria that are normally present in or on the body of an animal or growth of bacteria that are not normally present in or on the animal. More generally, a bacterial infection can be any situation in which the presence of a bacterial population(s) is damaging to a host animal. Thus, an animal is "suffering" from a bacterial infection when an excessive amount of a bacterial population is present in or on the animal's body, or when the presence of a bacterial population(s) is damaging the cells or other tissue of the animal.

By "chronic disease" is meant a disease that is inveterate, of long continuance, or progresses slowly, in contrast to an acute disease, which rapidly terminates. A chronic disease may begin with a rapid onset or in a slow, insidious manner but it tends to persist for several weeks, months or years, and has a vague and indefinite termination.

By "immunocompromised" is meant a person who exhibits an attenuated or reduced ability to mount a normal cellular or humoral defense to challenge by infectious agents, e.g., viruses, bacterial, fungi, and protozoa. Persons considered immunocompromised include malnourished patients, patients undergoing surgery and bone narrow transplants, patients undergoing chemotherapy or radiotherapy, neutropenic patients, HIV-infected patients, trauma patients, burn patients, patients with chronic or resistant infections such as those resulting from myelodysplastic syndrome, and the elderly, all of who may have weakened immune systems.

By "inflammatory disease" is meant a disease state characterized by (1) alterations in vascular caliber that lead to an increase in blood flow, (2) structural changes in the microvasculature that permit the plasma proteins and leukocytes to leave the circulation, and (3) emigration of the leukocytes from the microcirculation and their accumulation in the focus of injury. The classic signs of acute inflammation are erythema, edema, tenderness (hyperalgesia), and pain. Chronic inflammatory diseases are characterized by infiltration with mononuclear cells (e.g., macrophages, lymphocytes, and plasma cells), tissue destruction, and fibrosis. Non-limiting examples of inflammatory disease include asthma, coronary artery disease, arthritis, conjunctivitis, lymphogranuloma venerum, and salpingitis.

By "intracytoplasmic inclusion" is meant a replicating reticulate body (RB) that has no cell wall. Such inclusions may be detected, for example, through chlamydiae sample isolation and propagation on mammalian cell lines, followed by fixing and staining using one of a variety of staining methods including Giemsa staining, iodine staining, and immunofluorescence. These inclusions have a typical round or oval appearance.

By "persistent bacterial infection" is meant an infection that is not completely eradicated through standard treatment regimens using anti-bacterial agents. Persistent bacterial infections are caused by bacteria capable of establishing a cryptic or latent phase of infection and may be classified as such by culturing the bacteria from a patient and demonstrating bacterial survival in vitro in the presence of anti-bacterial agents or by determination of anti-bacterial treatment failure in a patient. As used herein, a persistent infection in a patient includes any recurrence of chlamydial infection, after receiving anti-bacterial treatment, from the same species (e.g., *C. trachomatis*) more than two times over the period of two or more years or the detection of the cryptic phase of the infection in the patient by the methods described. An in vivo persistent infection can be identified through the use of a reverse transcriptase polymerase chain reaction (RT-PCR) to demonstrate the presence of 16S rRNA transcripts in bacterially infected cells after treatment with anti-bacterial agents (*Antimicrob. Agents Chemother.* 12:3288-3297, 2000).

By "replicating phase" is meant the phase of the bacterial cell cycle characterized by the presence of an RB. The RB is the actively replicating form of the *Chlamydia*. It contains no cell wall and is detected as an inclusion in the cell.

As used herein, the term "treating" refers to administering or prescribing a pharmaceutical composition for prophylactic and/or therapeutic purposes. To "prevent disease" refers to prophylactic treatment of a patient who is not yet ill, but who is susceptible to, or otherwise at risk of, a particular disease. To "treat disease" or use for "therapeutic treatment" refers to administering treatment to a patient already suffering from a disease to improve the patient's condition. Thus, in the claims and embodiments, treating is the administration to an animal either for therapeutic or prophylactic purposes. An ear infection has been treated when one or more tests of the disease (e.g., any of the those described below) indicate that the patient's condition has improved. The detection of an infection may be done by a pneumatic otoscopic examination of the patient, or by a reduction in infection-associated symptoms in the patient (e.g., inflammation of ear drums, redness of ear drums, presence of fluid in ears). Reduction of symptoms may also be determined, for example, by audiogram to check recovery from hearing loss. Prophylactic administration of a compound of the invention is considered to be preventing the development of an ear infection.

By "effective amount" is meant the amount of a compound required to treat or prevent an infection. The effective amount of active compound(s) used to practice the present invention for therapeutic or prophylactic treatment of conditions caused by or contributed to by a microbial infection varies depending upon the manner of administration, the age, body weight, and general health of the subject. Ultimately, the attending physician or veterinarian will decide the appropriate amount and dosage regimen. Such amount is referred to as an "effective" amount.

The term "microbial infection" refers to the invasion of the host animal by pathogenic microbes. This includes the excessive growth of microbes that are normally present in or on the body of an animal. More generally, a microbial infection can be any situation in which the presence of a microbial population(s) is damaging to a host animal. Thus, an animal is "suffering" from a microbial infection when excessive numbers of a microbial population are present in or on an animal's body, or when the presence of a microbial population(s) is damaging the cells or other tissue of an animal.

The term "microbes" includes, for example, bacteria, fungi, yeasts, viruses and protozoa.

By "intracellular pathogen" is meant an infection by any facultative or obligate intracellular microbe.

By "obligate intracellular pathogen" is meant a microbe that must use an intracellular location (e.g., a host cell) in order to replicate.

By "facultative intracellular pathogen" is meant a microbe that is able to survive within an intracellular location (e.g., a host cell), but does not require an intracellular environment to replicate.

The term "administration" or "administering" refers to a method of giving a dosage of a pharmaceutical composition to an animal, where the method is, e.g., topical, oral, intravenous, intraperitoneal, or intramuscular. The preferred method of administration can vary depending on various factors, e.g., the components of the pharmaceutical composition, site of the potential or actual disease, and severity of disease.

The terms "animal," "subject," and "patient" specifically include humans, cattle, horses, dogs, cats, and birds, but also can include many other species.

DETAILED DESCRIPTION

Figure 1:
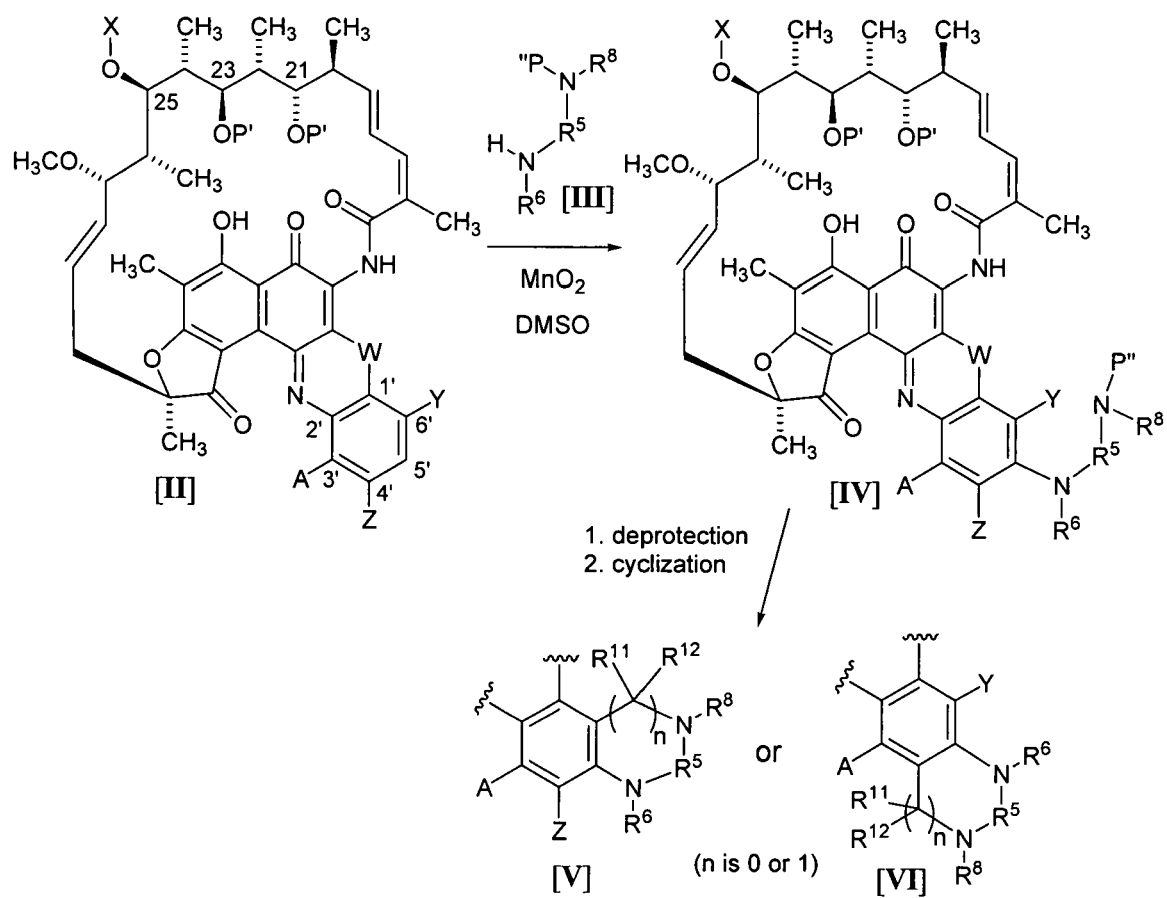
FIG. 1 is a synthetic scheme showing procedures to produce compounds of the present invention, as described in Example 1.

We have discovered novel rifamycin analogs and their use for treating or preventing a variety of microbial infections. The compounds of the present invention are described by formula I:

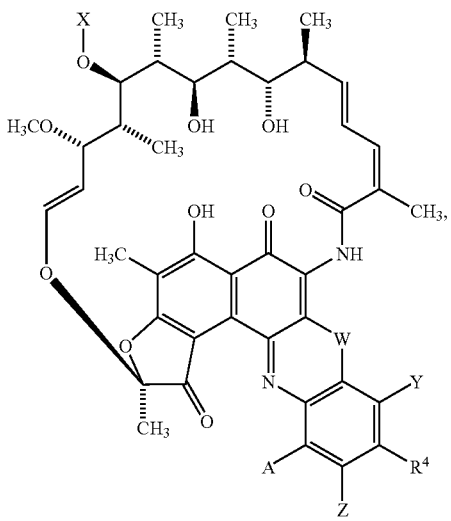

(I)

or a pharmaceutically acceptable salt thereof, wherein (a) A is H, OH, O—($C_1$-$C_6$ alkyl), O—($C_1$-$C_4$ alkaryl), O—($C_6$-$C_{12}$ aryl), O—($C_1$-$C_9$ heteroaryl), or O—($C_1$-$C_4$ alkheteroaryl);

W is O, S, or $NR^1$, wherein $R^1$ is H, $C_1$-$C_6$ alkyl, $C_1$-$C_4$ alkaryl, or $C_1$-$C_4$ alkheteroaryl;

X is H or $COR^2$, wherein $R^2$ is $C_1$-$C_6$ alkyl, which can be substituted with 1-5 OH groups, O—($C_3$-$C_7$ alkyl), which can be substituted with 1-4 OH groups, $C_6$-$C_{12}$ aryl, $C_1$-$C_4$ alkaryl, $C_1$-$C_9$ heteroaryl, or $C_1$-$C_4$ alkheteroaryl, wherein each alkyl carbon is bonded to no more than one oxygen atom;

Y is H, Hal, or $OR^3$, wherein $R^3$ is $C_1$-$C_6$ alkyl, $C_6$-$C_{12}$ aryl, $C_1$-$C_4$ alkaryl, $C_1$-$C_9$ heteroaryl, or $C_1$-$C_4$ alkheteroaryl;

$R^4$ is $OR^5$, $SR^5$, or $NR^5R^6$, wherein $R^5$ is defined below in relation to $R^7$ and $R^6$ is H, $C_1$-$C_6$ alkyl, $C_6$-$C_{12}$ aryl, $C_1$-$C_4$ alkaryl, $C_1$-$C_9$ heteroaryl, or $C_1$-$C_4$ alkheteroaryl, $COR^9$, $CO_2R^9$, $CONHR^9$, $CSR^9$, $COSR^9$, $CSOR^9$, $CSNHR^9$, $SO_2R^9$, or $SO_2NHR^9$, wherein $R^9$ is $C_1$-$C_6$ alkyl, $C_6$-$C_{12}$ aryl, $C_1$-$C_4$ alkaryl, heteroaryl, or $C_1$-$C_4$ alkheteroaryl; and Z is $(CR^{11}R^{12})_n NR^7R^8$, wherein n is 0 or 1, $R^7$ and $R^5$ together represent a bond or form a substituted or unsubstituted $C_1$-$C_4$ linkage, $R^8$ is H, $C_1$-$C_6$ alkyl, $C_6$-$C_{12}$ aryl, $C_1$-$C_4$ alkaryl, $C_1$-$C_9$ heteroaryl, or $C_1$-$C_4$ alkheteroaryl, $COR^{10}$, $CO_2R^{10}$, $CONHR^{10}$, $CSR^{10}$, $COSR^{10}$, $CSOR^{10}$, $CSNHR^{10}$, $SO_2R^{10}$, or $SO_2NHR^{10}$, wherein $R^{10}$ is $C_1$-$C_6$ alkyl, $C_6$-$C_{12}$ aryl, $C_1$-$C_4$ alkaryl, $C_1$-$C_9$ heteroaryl, or $C_1$-$C_4$ alkheteroaryl, or $R^8$ does not exist and a double bond is formed between N and an $R^5$-$R^7$ $C_1$ carbon linkage, each of $R^{11}$ and $R^{12}$ is, independently, H, $C_1$-$C_6$ alkyl, $C_1$-$C_4$ alkaryl, or $C_1$-$C_4$ alkheteroaryl, or $R^{12}$ does not exist and a double bond is formed between N and the carbon bearing $R^{11}$;

or (b) A is H, OH, O—($C_1$-$C_6$ alkyl), O—($C_1$-$C_4$ alkaryl), O—($C_6$-$C_{12}$ aryl), O—($C_1$-$C_9$ heteroaryl), or O—($C_1$-$C_4$ alkheteroaryl);

W is O, S, or $NR^1$, wherein $R^1$ is H, $C_1$-$C_6$ alkyl, $C_1$-$C_4$ alkaryl, or $C_1$-$C_4$ alkheteroaryl;

X is H or $COR^2$, wherein $R^2$ is $C_1$-$C_6$ alkyl, which can be substituted with 1-5 OH groups, O—($C_3$-$C_7$ alkyl), which can be substituted with 1-4 OH groups, $C_6$-$C_{12}$ aryl, $C_1$-$C_4$ alkaryl, $C_1$-$C_9$ heteroaryl, or $C_1$-$C_4$ alkheteroaryl, wherein each alkyl carbon is bonded to no more than one oxygen atom;

Z is H, Hal, or $OR^3$, wherein $R^3$ is $C_1$-$C_6$ alkyl, $C_6$-$C_{12}$ aryl, $C_1$-$C_4$ alkaryl, $C_1$-$C_9$ heteroaryl, or $C_1$-$C_4$ alkheteroaryl;

$R^4$ is $OR^5$, $SR^5$, or $NR^5R^6$, wherein $R^5$ is defined below in relation to $R^7$ and $R^6$ is H, $C_1$-$C_6$ alkyl, $C_6$-$C_{12}$ aryl, $C_1$-$C_4$ alkaryl, $C_1$-$C_9$ heteroaryl, or $C_1$-$C_4$ alkheteroaryl, $COR^9$, $CO_2R^9$, $CONHR^9$, $CSR^9$, $COSR^9$, $CSOR^9$, $CSNHR^9$, $SO_2R^9$, or $SO_2NHR^9$, wherein $R^9$ is $C_1$-$C_6$ alkyl, $C_6$-$C_{12}$ aryl, $C_1$-$C_4$ alkaryl, heteroaryl, or $C_1$-$C_4$ alkheteroaryl; and Y is $(CR^{11}R^{12})_n NR^7R^8$, wherein n is 0 or 1, $R^7$ and $R^5$ together represent a bond or form a substituted or unsubstituted $C_1$-$C_4$ linkage, $R^8$ is H, $C_1$-$C_6$ alkyl, $C_6$-$C_{12}$ aryl, $C_1$-$C_4$ alkaryl, $C_1$-$C_9$ heteroaryl, or $C_1$-$C_4$ alkheteroaryl, $COR^{10}$, $CO_2R^{10}$, $CONHR^{10}$, $CSR^{10}$, $COSR^{10}$, $CSOR^{10}$, $CSNHR^{10}$, $SO_2R^{10}$, or $SO_2NHR^{10}$, wherein $R^{10}$ is $C_1$-$C_6$ alkyl, $C_6$-$C_{12}$ aryl, $C_1$-$C_4$ alkaryl, $C_1$-$C_9$ heteroaryl, or $C_1$-$C_4$ alkheteroaryl, or $R^8$ does not exist and a double bond is formed between N and an $R^5$-$R^7$ $C_1$ carbon linkage, each of $R^{11}$ and $R^{12}$ is, independently, H, $C_1$-$C_6$ alkyl, $C_1$-$C_4$ alkaryl, or $C_1$-$C_4$ alkheteroaryl, or $R^{12}$ does not exist and a double bond is formed between N and the carbon bearing $R^{11}$.

We have also identified a method of preventing, stabilizing, or inhibiting the growth of microbes, or killing microbes, by contacting microbes or a site susceptible to microbial growth with a compound of the invention. Compounds of the present invention can be used to treat, stabilize, or prevent a microbial infection in an animal. In this method, the step of contacting microbes or a site susceptible to microbial infection (e.g., a site in or on the body of an animal) with a compound of the invention includes administering to the animal the compound in an amount sufficient to treat, stabilize, or prevent the microbial infection in the animal. In a related aspect, the invention features a method of treating any disease associated with such a microbial infection.

Compounds of the present invention can be used to treat atherosclerosis or diseases associated therewith, sexually transmitted diseases caused, for example, by *C. trachomatis* or *N. gonorrhoeae*, otitis media and other ear infections, antibiotic-associated colitis, gastritis and ulcers associated with an infection of *H. pylori*, Gram-positive infections, community-acquired pneumonia, upper and lower respiratory tract infections, skin and soft tissue infections, bone and joint infections, hospital-acquired lung infections, urinary tract infections, pyelonephritis, intra-abdominal infections, bacteremia, bacterial sepsis, would infections, peritonitis, osteomyelitis, infections after burns, pelvic inflammatory disease, and diseases associated with chronic infections.

Atherosclerosis and Other Diseases Associated with Chlamydial Infection

An association was previously reported in International Publication No. WO 98/50074 between the cryptic phase of a persistent chlamydial infection of body fluids and/or tissues and several chronic disease syndromes of previously unknown etiology in humans. To date, these diseases include, but are not limited to, atherosclerosis, multiple sclerosis, rheumatoid arthritis, inflammatory bowel disease, interstitial cystitis, fibromyalgia, autonomic nervous dysfunction (neural-mediated hypotension); pyoderma gangrenosum, and chronic fatigue syndrome.

As described in International Publication No. WO 98/50074, several lines of evidence have led to the establishment of a link between *Chlamydia* and a broad set of inflammatory, autoimmune, and immune deficiency diseases. These include (i) the association between the cryptic phase of a persistent chlamydial infection of body fluids and/or tissues and several chronic disease syndromes as described above, (ii) published evidence of an association between atherosclerosis and *Chlamydia* (*Circulation*, 96:404-407, 1997), and (iii) an understanding of the impact the persistent infection established by the cryptic phase of chlamydial infections can have on infected cells and the immune system. Thus, the present invention describes methods for treating chronic diseases associated with the cryptic phase of a persistent chlamydial infection, such as autoimmune diseases, inflammatory diseases and diseases that occur in immunocompromised individuals by treating the cryptic phase of the infection in an individual in need thereof, using the rifamycin analogs described herein. Progress of the treatment can be evaluated, using the diagnostic tests described herein, to determine the presence or absence of *Chlamydia*. Physical improvement in the conditions and symptoms typically associated with the disease to be treated can also be evaluated. Based upon these evaluating factors, the physician can maintain or modify the anti-bacterial therapy accordingly.

The therapies described herein can be used for the treatment of chronic immune and autoimmune diseases when patients are demonstrated to have a *Chlamydia* load by the methods of detection described above. These diseases include, but are not limited to, chronic hepatitis, systemic lupus erythematosus, arthritis, thyroidosis, scleroderma, diabetes mellitus, Graves' disease, Behcet's disease, and graft versus host disease (graft rejection). The therapies of this invention can also be used to treat any disorders in which a chlamydial species is a factor or co-factor.

Thus, the present invention can be used to treat a range of disorders in addition to the above immune and autoimmune diseases when demonstrated to be associated with chlamydial infection by the methods of detection described herein; for example, various infections, many of which produce inflammation as primary or secondary symptoms, including, but not limited to, sepsis syndrome, cachexia, circulatory collapse and shock resulting from acute or chronic bacterial infection, acute and chronic parasitic and/or infectious diseases from bacterial, viral or fungal sources, such as a HIV, AIDS (including symptoms of cachexia, autoimmune disorders, AIDS dementia complex and infections) can be treated, as well as Wegners Granulomatosis.

Among the various inflammatory diseases, there are certain features that are generally agreed to be characteristic of the inflammatory process. These include fenestration of the microvasculature, leakage of the elements of blood into the interstitial spaces, and migration of leukocytes into the inflamed tissue. On a macroscopic level, this is usually accompanied by the familiar clinical signs of erythema, edema, tenderness (hyperalgesia), and pain. Inflammatory diseases, such as chronic inflammatory pathologies and vascular inflammatory pathologies, including chronic inflammatory pathologies such as aneurysms, hemorrhoids, sarcoidosis, chronic inflammatory bowel disease, ulcerative colitis, and Crohn's disease and vascular inflammatory pathologies, such as, but not limited to, disseminated intravascular coagulation, atherosclerosis, and Kawasaki's pathology are also suitable for treatment by methods described herein. The invention can also be used to treat inflammatory diseases such as coronary artery disease, hypertension, stroke, asthma, chronic hepatitis, multiple sclerosis, peripheral neuropathy, chronic or recurrent sore throat, laryngitis, tracheobronchitis, chronic vascular headaches (including migraines, cluster headaches and tension headaches), and pneumonia.

Treatable disorders when associated with a chlamydial infection also include, but are not limited to, neurodegenerative diseases, including, but not limited to, demyelinating diseases, such as multiple sclerosis and acute transverse myelitis; extrapyramidal and cerebellar disorders, such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; progressive supranucleo palsy; cerebellar and spinocerebellar disorders, such as astructural lesions of the cerebellum; spinocerebellar degenerations (spinal ataxia, Friedreich's ataxia, cerebellar cortical degenerations, multiple systems degenerations (Mencel, Dejerine-Thomas, Shi-Drager, and Machado Joseph)); and systemic disorders (Refsum's disease, abetalipoprotemia, ataxia, telangiectasia, and mitochondrial multisystem disorder); demyelinating core disorders, such as multiple sclerosis, acute transverse myelitis; disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; senile dementia of Lewy body type; Wernicke-Korsakoff syndrome; chronic alcoholism; Creutzfeldt-Jakob disease; subacute sclerosing panencephalitis, Hallerrorden-Spatz disease; and Dementia pugilistica, or any subset thereof.

It is also recognized that malignant pathologies involving tumors or other malignancies, such as, but not limited to leukemias (acute, chronic myelocytic, chronic lymphocytic and/or myelodyspastic syndrome); lymphomas (Hodgkin's and non-Hodgkin's lymphomas, such as malignant lymphomas (Burkitt's lymphoma or mycosis fungoides)); carcinomas (such as colon carcinoma) and metastases thereof; cancer-related angiogenesis; infantile hemangiomas; and alcohol-induced hepatitis. Ocular neovascularization, psoriasis, duodenal ulcers, and angiogenesis of the female reproductive tract can also be treated when demonstrated by the diagnostic procedures described herein to be associated with a chlamydial infection.

Ear Infections

Ear infections typically affect the middle or the external ear and include, for example, otitis media, otitis externa, and infections caused by surgical interventions. Due to multiplicity of secondary complications that arise from ear infections such as hearing loss, the treatment and prevention of such conditions is critical.

Topical administration of a compound of formula I is effective in treating or preventing an infection of the ear, such as otitis media or otitis externa. In the case of otitis media or externa, infections are primarily caused by *H. influenza, M. catarhalis, S. pneumoniae, S. pyogenes, S. intermedius, S. epidermidis, S. aureus, S. caprae, S. auriculis, S. capitis, S. haemolytis, P. aeroginosa, P. mirabilis, P. vulgaris, E. faecalis*, or *E. coli*. A compound of formula I can be used to treat each of these infections of the ear. A compound of formula I may, for example, be topically administered to the area of the ear to which surgical intervention was performed or, alternatively, the compound may be administered to the ear of the patient prophylactically, prior to otic surgery, noninvasive otic procedures, or other types of surgery. Exemplary surgical procedures include for example, cochlear implant surgery, tympanoplasty, tympanostomy tube insertion, removal of tumors (e.g., cholesteatoma), or stapedectomy. The compound may be administered to the area of the ear to which surgical intervention will be performed, for example, within seven days, two days, one day, 12 hours, 10 hours, 6 hours, 4 hours, 2 hours, 1 hour, or less than 1 hour prior to or following the surgical intervention. The compositions may be used for acute treatment of temporary conditions, or may be administered chronically.

A compound of formula I may be given daily (e.g., once, twice, three times, or four times daily) or less frequently (e.g., once every other day, or once or twice weekly). Typically, patients are administered a dosage consisting of one to four drops of solution containing the compound. The compound may be contained in any appropriate amount in any suitable carrier substance, and is generally present in an amount between 0.001% and 5%, desirably 0.01% and 3%, more desirably 0.1% and 1%, and even more desirably 0.1% and 0.4% by weight of the total volume (w/v) of the composition. The compound is provided in a dosage form that is suitable for topical administration. Thus, a composition containing a compound of formula I may be in the form of a solution, aerosol, gel, ointment, nebulizer, or suspension. Alternatively, a compound of the invention may be administered by placing an impregnated porous media into the external ear canal to the tympanic membrane. The pharmaceutical composition can generally be formulated according to conventional pharmaceutical practice.

Aural Toilet

The external auditory canal and tissues lateral to the infected middle ear often are covered with mucoid exudate or desquamated epithelium. Since topically applied preparations cannot generally penetrate affected tissues until these interposing materials are removed, aural toilet is desirably performed before administering a compound of formula I. Aural toilet may be performed by a health provider, the patient, or any other individual. Removal of debris may be performed mechanically with the assistance of a microscope and microinstruments. Aural irrigation may also be performed using a solution containing peroxide. The concentration of peroxide should be the highest concentration without causing significant pain, or discomfort, to the patient. As an example, a solution of 50% peroxide and 50% sterile water can be used. Thirty to 40 mL of this solution can be irrigated through the external auditory canal, using a small syringe or bulb-type aspirator. The irrigant solution is allowed to drain out (e.g., for 5-10 minutes) prior to administering a compound of the invention.

Granulation Tissue

Granulation tissue often fills the middle ear and medial portions of the external auditory canal, and reducing this accumulation is beneficial for resolution of an ear infection. Granulation tissue may also prevent topically applied antimicrobial agents from penetrating to the site of infection, and the amount of granulation tissue is desirably reduced throughout the regimen.

Although topical antimicrobial drops can reduce granulation by eliminating infection and by removing the inciting irritating inflammation, the amount of granulation tissue may be reduced using other methods known in the art. For example, topical steroids may hasten the resolution of middle ear granulation, thus improving penetration of topically delivered antibiotics.

Cautery may also be used to reduce the amount of granulation tissue and to reduce its formation. Microbipolar cautery may be administered by a health provider. Chemical cautery, using for example silver nitrate, may also be applied to an infected ear in the form of silver nitrate sticks. Excision of granulation tissue may also be performed by a health care provider with a microscope and microinstruments.

Ear Canal Acidification

In a patient affected with otitis externa, a therapy involving ear canal acidification to restore the physiological acidity of the ear may be performed. The affected ear is administered with a solution containing acetic acid, which may also include a steroid (e.g., hydrocortisone), aluminum acetate, or rubbing alcohol.

Topical Formulations

Pharmaceutical compositions according to the present invention can be formulated for topical administration to the ear of the patient. Patients having an ear infection may be administered with effective amounts of a compound of the invention, by means of a solution (e.g., drops), ointment, gel, or aerosol (e.g., nebulizer). The composition is typically administered to the affected otic area by topically applying, for example, one to four drops of a solution or suspension, or a comparable amount of an ointment, gel, or other solid or semisolid composition, once, twice, three times, or more than three times per day. A porous media or an ear wick (e.g., cotton, gauze, or compressed hydroxycellulose) may also be used to increase the penetration of a compound of the invention to the infected otic area. The ear wick, which is inserted into the canal under direct vision, is typically a dried sponge that helps wick eardrops along the canal, hold the solution in contact with the skin of the canal and apply pressure to the canal skin. Wicks may be removed at one day, two days, or more than two days, and may be replaced if necessary. Alternatively, the ear wick may itself be impregnated with a compound of the invention. These formulations can be made according to known and conventional methods for preparing such formulations.

For compounds of the invention that are not highly soluble in water at physiological conditions, a solubilizing excipient may be used to increase solubility. Solubilization is taken to mean an improvement in the solubility by virtue of surface-active compounds that can convert substances that are insoluble or virtually insoluble in water into clear, or opalescent, aqueous solutions without changing the chemical structure of these substances in the process. Excipients used for this purpose are restricted to those that are safe for administration to humans. Typically such co-solvents are employed at a level of about 0.01% to 2% by weight.

A variety of solubilizing excipients may be used for the formulation of a compound of the invention, including compounds belonging to the following classes: polyethoxylated fatty acids, PEG-fatty acid diesters, PEG-fatty acid monoester and di-ester mixtures, polyethylene glycol glycerol fatty acid esters, alcohol-oil transesterification products, polyglycerized fatty acids, propylene glycol fatty acid esters, mixtures of propylene glycol esters and glycerol esters, mono- and diglycerides, sterol and sterol derivatives, polyethylene glycol sorbitan fatty acid esters, polyethylene glycol alkyl ethers, sugar esters, polyethylene glycol alkyl phenols, polyoxyethylene-polyoxypropylene block copolymers, sorbitan fatty acid esters, lower alcohol fatty acid esters, or ionic surfactants. Such excipients are described for example, in U.S. Patent Application No. 60/385,532, hereby incorporated by reference.

Ototopical preparations may vary in viscosity. The use of viscosity enhancing agents to provide the compositions of the invention with viscosities greater than the viscosity of simple aqueous solutions may be desirable to increase the retention time in the ear. Such viscosity-building agents include, for example, polyvinyl alcohol, polyvinyl pyrrolidone, methyl cellulose, hydroxypropyl methylcellulose, hydroxyethyl cellulose, carboxymethyl cellulose, hydroxypropyl cellulose, or other agents known to those skilled in the art. Such agents are typically employed at a level of about 0.01% to 2% by weight. Optionally, these preparations may include a buffering agent to maintain an acidic pH, since the normal environment of the external auditory canal is acidic. However, if treatment is required in the middle ear where the pH is neutral, the pH can be adjusted accordingly.

Otic pharmaceutical products are typically packaged in multidose form. Preservatives are thus desired to prevent microbial contamination during use. Suitable preservatives include: polyquaternium-1, benzalkonium chloride, thimerosal, chlorobutanol, methyl paraben, propyl paraben, phenylethyl alcohol, edetate disodium, sorbic acid, or other agents known to those skilled in the art. Typically such preservatives are employed at a level of from 0.001% to 1.0% by weight.

A penetration enhancer may also be used to facilitate the diffusion of a compound of the invention through the tympanic membrane into the middle and inner ear in order to reduce inflammation of ear tissues. A penetration enhancer is an agent used to increase the permeability of the skin to a pharmacologically active agent to increase the rate at which the drug diffuses through the skin and enters the tissues and bloodstream. A chemical skin penetration enhancer increases skin permeability by reversibly damaging or by altering the physiochemical nature of the stratum corneum to reduce its diffusional resistance (Osborne D W, Henke J J, *Pharmaceutical Technology*, November 1997, pp 58-86). Examples of penetration enhancers include without limitation: alcohols, such as ethanol and isopropanol; polyols, such as n-alkanols, limonene, terpenes, dioxolane, propylene glycol, ethylene glycol, other glycols, and glycerol; sulfoxides, such as dimethylsulfoxide (DMSO), dimethylformamide, methyl dodecyl sulfoxide, dimethylacetamide; esters, such as isopropyl myristate/palmitate, ethyl acetate, butyl acetate, methyl proprionate, and capric/caprylic triglycerides; ketones; amides, such as acetamides; oleates, such as triolein; various surfactants, such as sodium lauryl sulfate; various alkanoic acids, such as caprylic acid; lactam compounds, such as azone; alkanols, such as oleyl alcohol; dialkylamino acetates, and admixtures thereof. The use of such penetration enhancers is disclosed, for example, in U.S. Pat. No. 6,093,417, hereby incorporated by reference.

Other Therapeutic Agents

Compositions containing a compound of the invention may also include a second therapeutic agent, such as, for example, another rifamycin analog, an anesthetic, an antimicrobial agent, a zinc salt, or an anti-inflammatory agent (e.g., an non-steroidal anti-inflammatory or a steroid). When admixing an antimicrobial agent, the antimicrobial agent is preferably penicillin G, penicillin V, methicillin, oxacillin, cloxacillin, dicloxacillin, nafcillin, ampicillin, amoxicillin, carbenicillin, ticarcillin, mezlocillin, piperacillin, azlocillin, temocillin, cepalothin, cephapirin, cephradine, cephaloridine, cefazolin, cefamandole, cefuroxime, cephalexin, cefprozil, cefaclor, loracarbef, cefoxitin, cefmatozole, cefotaxime, ceftizoxime, ceftriaxone, cefoperazone, ceftazidime, cefixime, cefpodoxime, ceftibuten, cefdinir, cefpirome, cefepime, BAL5788, BAL9141, imipenem, ertapenem, meropenem, astreonam, clavulanate, sulbactam, tazobactam, streptomycin, neomycin, kanamycin, paromycin, gentamicin, tobramycin, amikacin, netilmicin, spectinomycin, sisomicin, dibekalin, isepamicin, tetracycline, chlortetracycline, demeclocycline, minocycline, oxytetracycline, methacycline, doxycycline, erythromycin, azithromycin, clarithromycin, telithromycin, ABT-773, lincomycin, clindamycin, vancomycin, oritavancin, dalbavancin, teicoplanin, quinupristin and dalfopristin, sulphanilamide, para-aminobenzoic acid, sulfadiazine, sulfisoxazole, sulfamethoxazole, sulfathalidine, linezolid, nalidixic acid, oxolinic acid, norfloxacin, perfloxacin, enoxacin, ofloxacin, ciprofloxacin, temafloxacin, lomefloxacin, fleroxacin, grepafloxacin, sparfloxacin, trovafloxacin, clinafloxacin, gatifloxacin, moxifloxacin, gemifloxacin, sitafloxacin, metronidazole, daptomycin, garenoxacin, ramoplanin, faropenem, polymyxin, tigecycline, AZD2563, or trimethoprim. Preferred non-steroidal anti-inflammatory agents include, for example, detoprofen, diclofenac, diflunisal, etodolac, fenoprofen, flurbiprofen, indomethacin, ketoprofen, mechlofenameate, mefenamic acid, meloxicam, nabumeone, naproxen sodium, oxaprozin, piroxicam, sulindac, tolmeting, celecoxib, rofecoxib, choline salicylate, salsate, sodium salicylate, magnesium salicylate, aspirin, ibuprofen, paracetamol, acetaminophen, and pseudoephedrine, and preferred steroids include, for example, hydrocortisone, prednisone, fluprednisolone, triamcinolone, dexamethasone, betamethasone, cortisone, prednilosone, methylprednisolone, fluocinolone acetonide, flurandrenolone acetonide, and fluorometholone. Preferred anesthetics according to the invention include, for example, benzocaine, butamben picrate, tetracaine, dibucaine, prilocalne, etidocaine, mepivacaine, bupivicaine, and lidocaine. A zinc salt can be zinc sulfate, zinc chloride, zinc acetate, zinc phenol sulfonate, zinc borate, zinc bromide, zinc nitrate, zinc glycerophosphate, zinc benzoate, zinc carbonate, zinc citrate, zinc hexafluorosilicate, zinc diacetate trihydrate, zinc oxide, zinc peroxide, zinc salicylate, zinc silicate, zinc stannate, zinc tannate, zinc titanate, zinc tetrafluoroborate, zinc gluconate, or zinc glycinate. All of the therapeutic agents employed in the compositions of the present invention can be used in the dose ranges currently known and used for these agents.

Different concentrations may be employed depending on the clinical condition of the patient, the goal of therapy (treatment or prophylaxis), the anticipated duration, and the severity of the infection for which a compound of the invention is being administered. Additional considerations in dose selection include the type of infection, age of the patient (e.g., pediatric, adult, or geriatric), general health, and comorbidity.

Synthesis

Compounds of formula I can be synthesized by methods analogous to those disclosed in U.S. Pat. Nos. 4,610,919; 4,983,602; 5,786,349; 5,981,522; and 4,859,661, and *Chem. Pharm. Bull.*, 41:148, 1993, each of which is hereby incorporated by reference. Non-limiting methods used for the preparation of individual compounds of the invention are provided in Examples 1-11.

Assays

Compounds of the present invention can be screened for antimicrobial activity by measuring their minimum inhibitory concentration (MIC), using standard MIC in vitro assays (see, for example, Tomioka et al., *Antimicrob. Agents Chemother.* 37:67, 1993. Agents can be screened against *C. pneumoniae, C. trachomatis, M. tuberculosis* (including multiple drug resistant strains), *M. avium* complex, and other intracellular infectious microbes. Details of a standard MIC assay are provided in Example 12.

Therapy

The invention features a method of treating or preventing a disease or condition associated with a microbial infection by administering a compound of formulas (I). Compounds of the present invention may be administered by any appropriate route for treatment or prevention of a disease or condition associated with a microbial infection, inflammation, or infection derived autoimmune disease. These may be administered to humans, domestic pets, livestock, or other animals with a pharmaceutically acceptable diluent, carrier, or excipient, in unit dosage form. Administration may be topical, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration.

Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in *Remington: The Science and Practice of Pharmacy* (20th ed., ed. A. R. Gennaro A R.), Lippincott Williams & Wilkins, 2000. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycholate and deoxycholate, or may be oily solutions for administration in the form of nasal drops, or as a gel.

The concentration of the compound in the formulation will vary depending upon a number of factors, including the dosage of the drug to be administered, and the route of administration.

The compound may be optionally administered as a pharmaceutically acceptable salt, such as a non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like.

Administration of compounds in controlled release formulations is useful where the compound of formula I has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window in the gastro-intestinal tract; or (iii) a short biological half-life, so that frequent dosing during a day is required in order to sustain the plasma level at a therapeutic level.

Many strategies can be pursued to obtain controlled release in which the rate of release outweighs the rate of metabolism of the therapeutic compound. For example, controlled release can be obtained by the appropriate selection of formulation parameters and ingredients (e.g., appropriate controlled release compositions and coatings). Examples include single or multiple unit tablet or capsule compositions, oil solutions, suspensions, emulsions, microcapsules, microspheres, nanoparticles, patches, and liposomes.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

Pharmaceutical formulations of compounds of the invention described herein include isomers such as diastereomers and enantiomers, mixtures of isomers, including racemic mixtures, salts, solvates, and polymorphs thereof.

Compounds of the invention may be used in combination with another antifungal, antiviral, antibacterial, or antiprotozoan compound or combinations thereof. The other agent may be employed as a supplemental antimicrobial for the purpose of broadening the activity spectrum of the therapeutics or to obtain particular effects, such as, to reduce the development of drug resistant microbes. Compounds of the invention can be used either alone or in conjunction with other pharmaceutical compounds to effectively combat a single infection. For example, compounds of the invention may be used either alone or combined with acyclovir in a combination therapy to treat HSV-1. Compounds of the invention may also be used either alone or in conjunction with other pharmaceutical compounds to combat multiple infections. For example, compounds of the invention may be used in combination with one or more anti-mycobacterial agents such as isoniazid, pyrazinamide, or ethambutol to treat or prevent intracellular bacterial infections.

Compounds of the invention may also be used in combination with Intron A and/or a biflavanoid for treating Hepatitis B; with gancyclovir, progancyclovir, famcyclovir, foscarnet, vidarabine, cidovir, and/or acyclovir for treating herpes viruses; and with ribavarin, amantidine, and/or rimantidine for treating respiratory viruses.

The following examples are put forth so as to provide those of ordinary skill in the art with a description of how the methods and compounds claimed herein are performed, made, and evaluated. The examples are intended to be purely exemplary and are not intended to limit the scope of what the inventors regard as their invention.

Syntheses of Benzoxazinorifamycin Compounds

Benzoxazinorifamycin compounds can be prepared using methods that require the selective protection and deprotection of alcohols, amines, sulfhydryls and/or carboxylic acid functional groups. For example, commonly used protecting groups for amines include carbamates, such as tert-butyl, benzyl, 2,2,2-trichloroethyl, 2-trimethylsilylethyl, 9-fluorenylmethyl, allyl, and m-nitrophenyl. Other commonly used protecting groups for amines include amides, such as formamides, acetamides, trifluoroacetamides, sulfonamides, trifluoromethanesulfonyl amides, trimethylsilylethanesulfonamides, and tert-butylsulfonyl amides. Examples of commonly used protecting groups for carboxylic acids include esters, such as methyl, ethyl, tert-butyl, 9-fluorenylmethyl, 2-(trimethylsilyl)ethoxy methyl, benzyl, diphenylmethyl, O-nitrobenzyl, ortho-esters, and halo-esters. Examples of commonly used protecting groups for alcohols include ethers, such as methyl, methoxymethyl, methoxyethoxymethyl, methylthiomethyl, benzyloxymethyl, tetrahydropyranyl, ethoxyethyl, benzyl, 2-napthylmethyl, O-nitrobenzyl, P-nitrobenzyl, P-methoxybenzyl, 9-phenylxanthyl, trityl (including methoxy-trityls), and silyl ethers.

Examples of commonly used protecting groups for sulfhydryls include many of the same protecting groups used for hydroxyls. In addition, sulfhydryls can be protected in an oxidized form (e.g., as disulfides, sulfonic acids, sulfonic esters, or sulfonic amides). Protecting groups can be chosen such that selective conditions (e.g., acidic conditions, basic conditions, catalysis by a nucleophile, catalysis by a Lewis acid, or hydrogenation) are required to remove each, exclusive of other protecting groups in a molecule. The conditions required for the addition of protecting groups to amine, alcohol, sulfhydryl, and carboxylic acid functionalities and the conditions required for their removal are provided in detail in T. W. Green and P. G. M. Wuts, *Protective Groups in Organic Synthesis* ($2^{nd}$ Ed.), John Wiley & Sons, 1991 and P. J. Kocienski, *Protecting Groups*, Georg Thieme Verlag, 1994 (hereby incorporated by reference). In the examples that follow, the use of protecting groups is indicated in a structure by the letter P, where P for any amine, carboxylic acid, sulfhydryl, or alcohol may be any of the protecting groups listed above.

EXAMPLE 1

General Coupling Procedure

The synthesis of benzoxazinorifamycin, benzthiazinorifamycin, and benzdiazinorifamycin analogs of the present invention can all proceed through the same general route as shown in FIG. 1, using the general methods disclosed in U.S. Pat. No. 4,965,261 for the attachment of amines to the 5'-position. In this scheme, rifamycin azaquinones of the formula II are dissolved in a suitable solvent, for example, DMSO, and reacted with amines or the formula III in the presence of manganese dioxide for several hours at room temperature to form azaquinones of the formula IV. If required, the azaquinones of the formula IV can be further reacted with deprotection reagents to remove X at the 25-position, P' at the 21 and 23 positions, any protecting group on Y or Z, and/or any P''' protecting group introduced with amines of the formula III. Once an amine of formula III has been attached to the benzoquinone and, if required, the necessary protecting groups removed, cyclization can be affected between the amine on $R^5$ and either carbon of the phenyl ring bearing the Y or Z substituent, respectively. The chemistry used for the cyclization can vary according to the functionality involved. In one example, when A is OH, Y and Z are each hydrogen, and the amine of formula III is symmetrical, both nitrogens of the amine can add to the phenyl ring to form compounds of formula V, where n is 0.

In some embodiments, the 25-position can be further derivatized with groups that introduce useful pharmacodynamic properties, such as groups that transform a rifamycin analog into a prodrug. Such groups are known to those skilled in the art, examples of which can be found in Testa and Mayer, *Hydrolysis in Drug and Prodrug Metabolism: Chemistry, Biochemistry and Enzymology*, published by Vch. Verlagsgesellschaft Mbh., 2003, which is hereby incorporated by reference.

Figure 2:
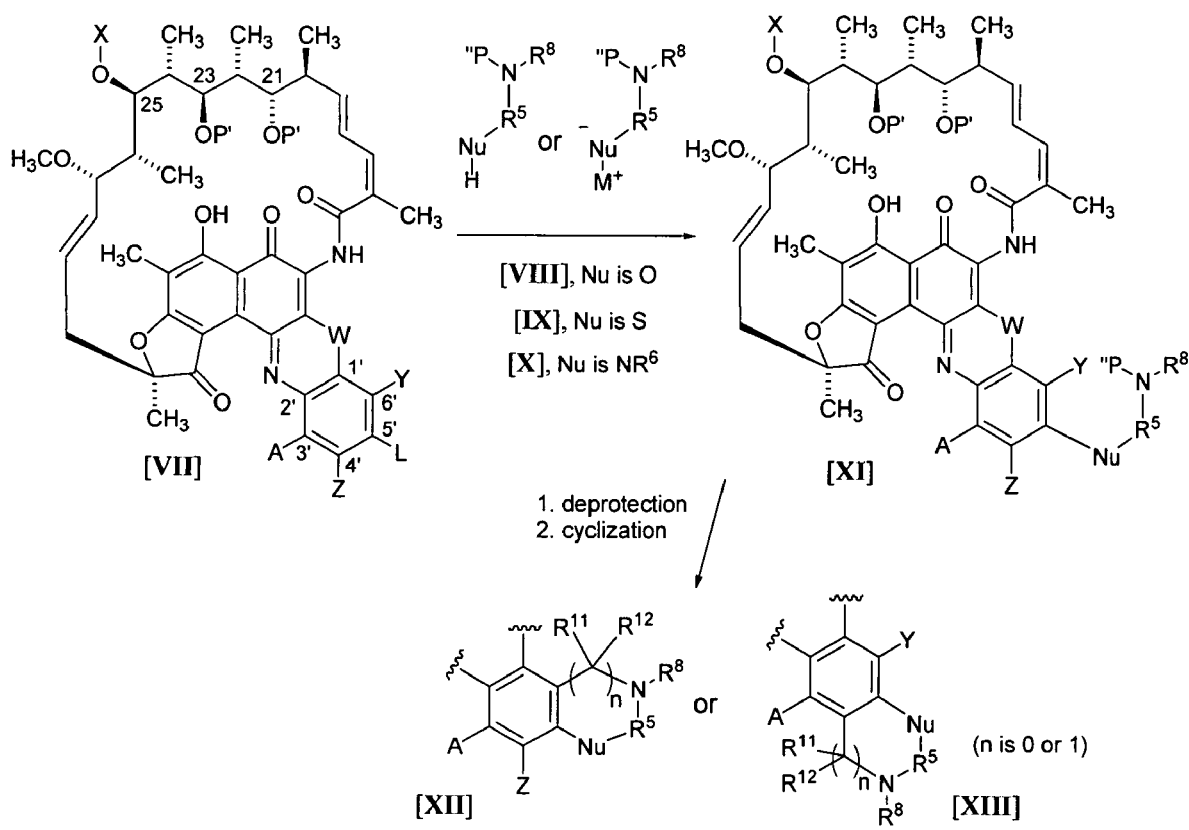
FIG. 2 is a synthetic scheme showing procedures to produce compounds of the present invention, as described in Example 1.

Alternatively, as shown in FIG. 2, azaquinones of formula VII, with a leaving group (L) at the 5' position can be reacted with an intermediate containing a nucleophilic oxygen, sulfur, or nitrogen moiety, represented by "Nu" in formulas VIII, IX, and X, respectively. L can be a halogen or a sulfonate, such as a triflate. After the heteroatom of the nucleophile has displaced the leaving group, cyclization of the $R^5$ pendant amine group can be accomplished as described above in the description of FIG. 1.

Figure 3:
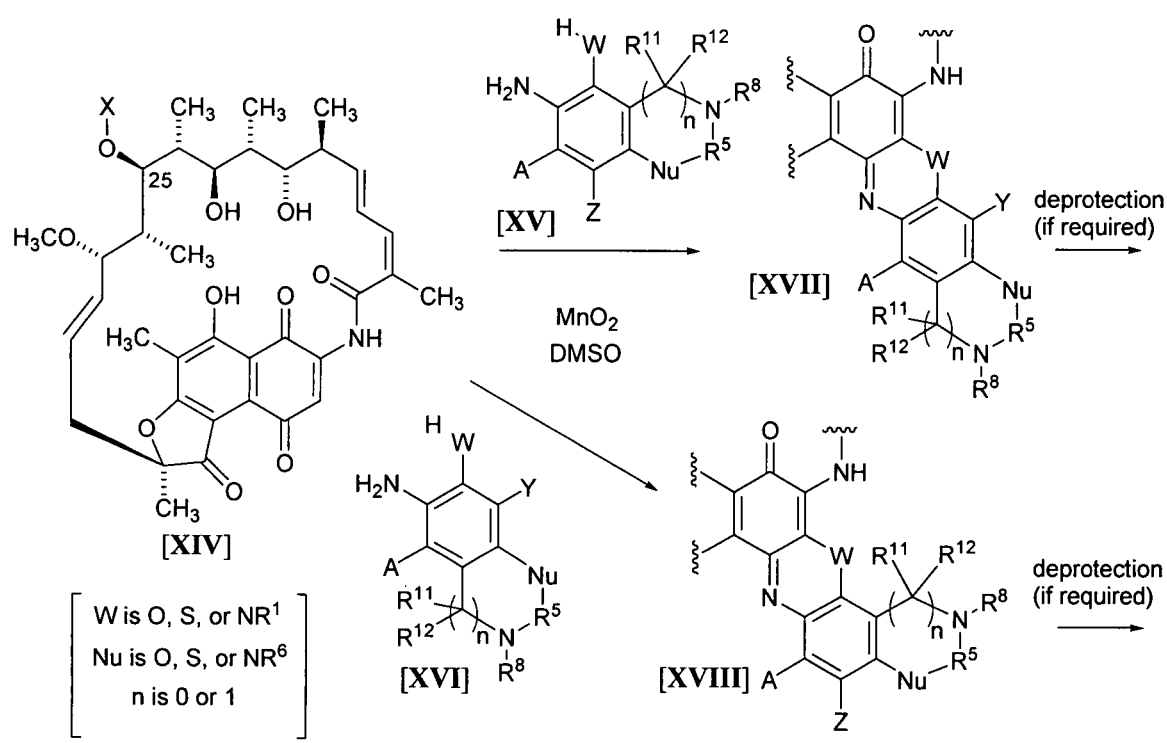
FIG. 3 is a synthetic scheme showing procedures to produce compounds of the present invention, as described in Example 1.

Alternatively, using the methods described in *Helv. Chim. Acta* 56:2369, 1973, rifamycin quinones of the formula (XIV) can be reacted with anilines with a hydroxyl, a sulfhydryl, or an amino group in the ortho position to produce azaquinones. One example, shown in FIG. 3, is the use of compounds of the formulas XV and XVI for the preparation of compounds of the formulas XVII and XVIII, respectively. Similarly, compounds 1002 (used in Example 9), 1003 (used in Example 10), and 1004 (used in Example 11) can be prepared by reacting the compound of formula XIV where X is $COCH_3$ with 2-amino-3,6-dimethylphenol, 2-amino-4,5-difluorophenol, and 2-amino-thiophenol, respectively.

EXAMPLE 2

General Deacetylation Procedure

Figure 4:
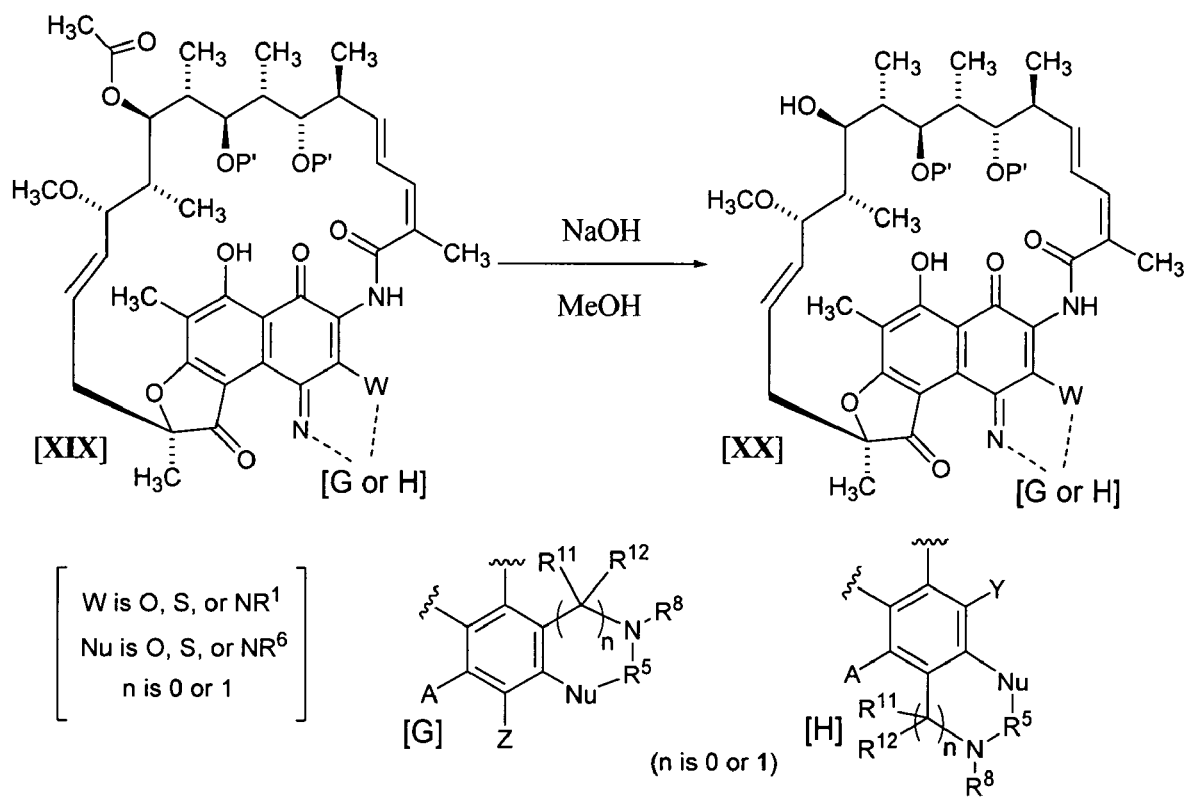
FIG. 4 is a synthetic scheme showing a deacetylation procedure to produce compounds of the present invention, as described in Example 2.

As shown in FIG. 4, compounds of the formula XIX (~100 mmol) were dissolved in methanol (5 mL) and treated with saturated sodium hydroxide in methanol solution (5 mL) for between 0.5 h to 3 h at rt. The reaction mixture was then poured into saturated ammonium chloride solution and extracted with chloroform. The organics were washed with water (2×) and dried over $Na_2SO_4$. Filtration, followed by removal of the solvent in vacuo, yielded des-acetyl products of the formula XX. If desired, these products were purified via flash chromatography (silica gel) using an appropriate solvent system, such as 1-10% methanol in methylene chloride.

EXAMPLE 3

Synthesis of Compound 1 (Tandem Coupling)

Figure 5:
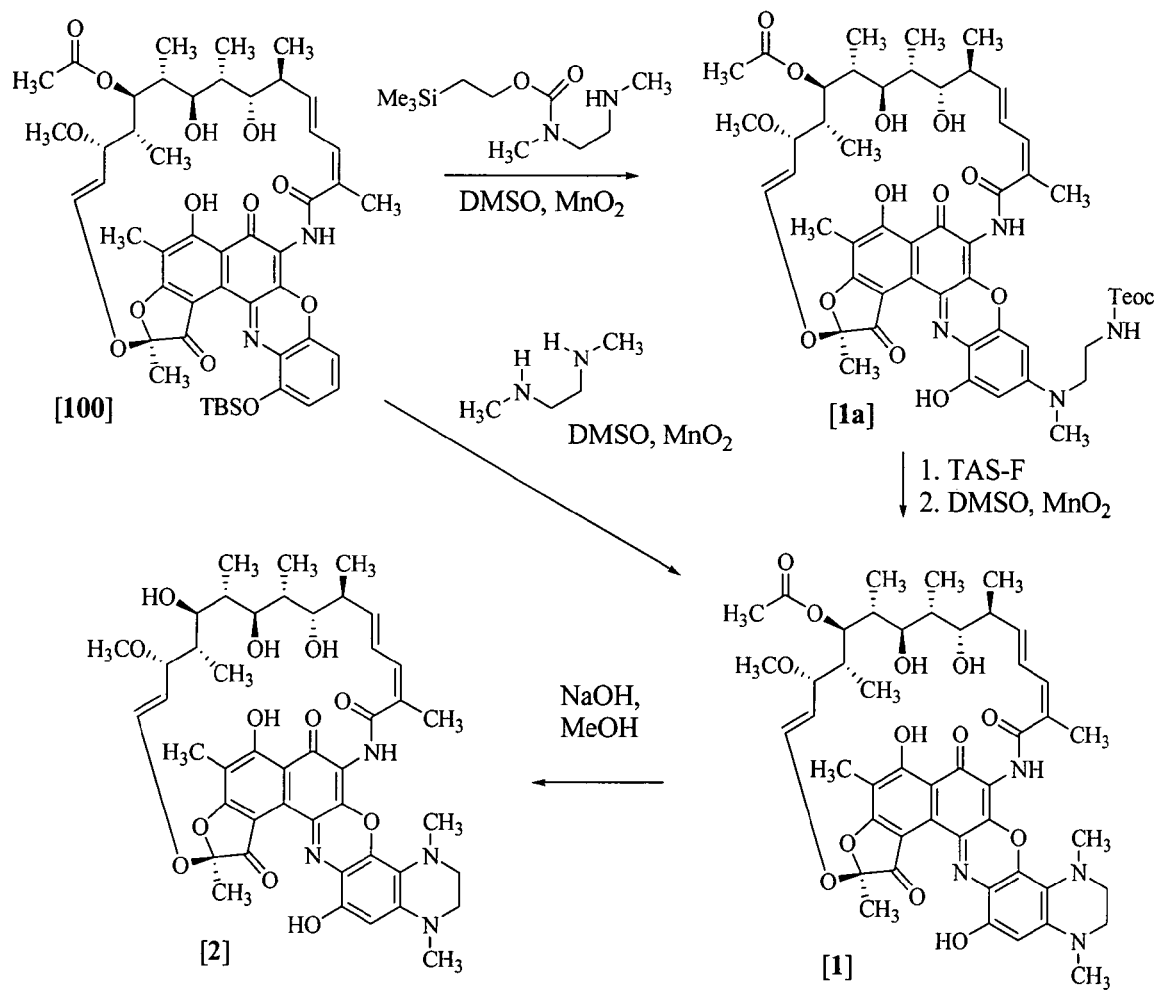
FIG. 5 is a synthetic scheme showing procedures to produce compounds 1, 1a, and 2, as described in Examples 3-5.

The title compound was prepared using a general coupling procedure of Example 1. Accordingly, as shown in FIG. 5, compound 100 (1.20 g, 1.31 mmol), N,N'-dimethylethyleneaminediamine (0.6 mL, 5 mmol), and manganese (IV) oxide (840 mg, 9.7 mmol) in 10 µL of DMSO were stirred at room temperature for 36 hours. The reaction was diluted with methylene chloride and filtered through Celite™. The resulting solution washed with water (3×) and dried over sodium sulfate. Filtration, followed by removal of the solvent in vacuo yielded a blue residue that was purified via MPLC (silica gel, gradient 0-2%, methanol in methylene chloride) to yield compound 1 as a blue solid (286 mg, 0.323 mmol, 25% yield); ESI (+) MS: 885 (M+H$^+$); TLC: $R_f$=0.35 (19:1, methylene chloride:methanol, Whatman MK6F, 60 angstrom); UV/Vis: $\lambda_{max}$=670.8 nm; and Mp 276-277° C.

EXAMPLE 4

Synthesis of Compound 1 (Stepwise Coupling)

N-(2-trimethylsilylethoxycarbonyl)-N,N'-dimethylethylenediamine was prepared as follows: to a stirred solution of N,N'-dimethylethylenediamine (616 mg, 5.94 mmol) and aqueous sodium carbonate (2M, 25 mL) at room temperature was added a solution of 2-(trimethylsilyl)ethyl-4-nitrophenyl carbonate (1.31 g, 4.63 mmol) in ethanol (15 mL). The reaction was heated at reflux for 1 h and then stirred at room temperature for 20 hours. The suspension was partially reduced in vacuo and the resulting slurry was added to water (100 mL) and extracted with methylene chloride (3×50 mL). The combined organics were filtered, dried over sodium sulfate and reduced in vacuo. The crude residue was purified via MPLC (silica gel, gradient 5-30%, methanol in methylene chloride) to yield N-(2-trimethylsilylethoxycarbonyl)-N,N'-dimethylethylenediamine as a light yellow solid (380 mg, 1.64 mmol, 35% yield); $^1$H NMR (CDCl$_3$, 300 MHz): δ 4.14 (m, 2H), 3.34 (m, 2H), 2.88 (s, 3H), 2.71 (m, 2H), 2.42 (s, 3H), 0.97 (m, 2H), 0.01 (s, 9H); ESI (+) MS: 233 (M+H$^+$); TLC: R$_f$=0.06 (4:1, methylene chloride:methanol, Whatman MK6F, 60 angstrom).

Using the mono-Teoc-protected diamine, the title compound was prepared using a general coupling procedure of Example 1. Accordingly, as shown in FIG. 5, compound 100 (608 mg, 0.664 mmol), N-(2-trimethylsilylethoxycarbonyl)-N,N'-dimethylethylenediamine (380 mg, 1.64 mmol), and manganese (IV) oxide (980 mg, 11.3 mmol) in 10 mL of DMSO were stirred at room temperature for 36 hours. The reaction was diluted with methylene chloride and filtered through Celite™. The resulting solution washed with water (3×) and dried over sodium sulfate. Filtration, followed by removal of the solvent in vacuo yielded a blue residue The resulting residue was purified via flash column chromatography (silica gel, gradient 60-80%, ethyl acetate in hexanes then 0-5% methanol in methylene chloride) to yield compound 1a as a blue solid (240 mg, 0.23 mmol, 35%). ESI (+) MS: 1031 (M+H$^+$). TLC: R$_f$=0.42 (19:1, methylene chloride:methanol, Whatman MK6F, 60 angstrom).

Compound 1a can be carried on to compound 1 by reacting it with tetrabutylammonium fluoride (TBAF, 1.05 equivalents) in DMF. After Teoc group removal the intermediate can be cyclized in the presence of air to compound 1.

EXAMPLE 5

Synthesis of Compound 2

As shown in FIG. 5, the title compound was prepared by the general deacetylation procedure of Example 2 using compound 1 (240 mg, 0.271 mmol) to provide compound 2 (104 mg, 45% yield) as a blue solid, Mp=234-240° C.; ESI (+) MS: 843 (M+H$^+$); UV/Vis: $\lambda_{max}$=670.5 nm.

EXAMPLE 6

Synthesis of Compound 3

Figure 6:
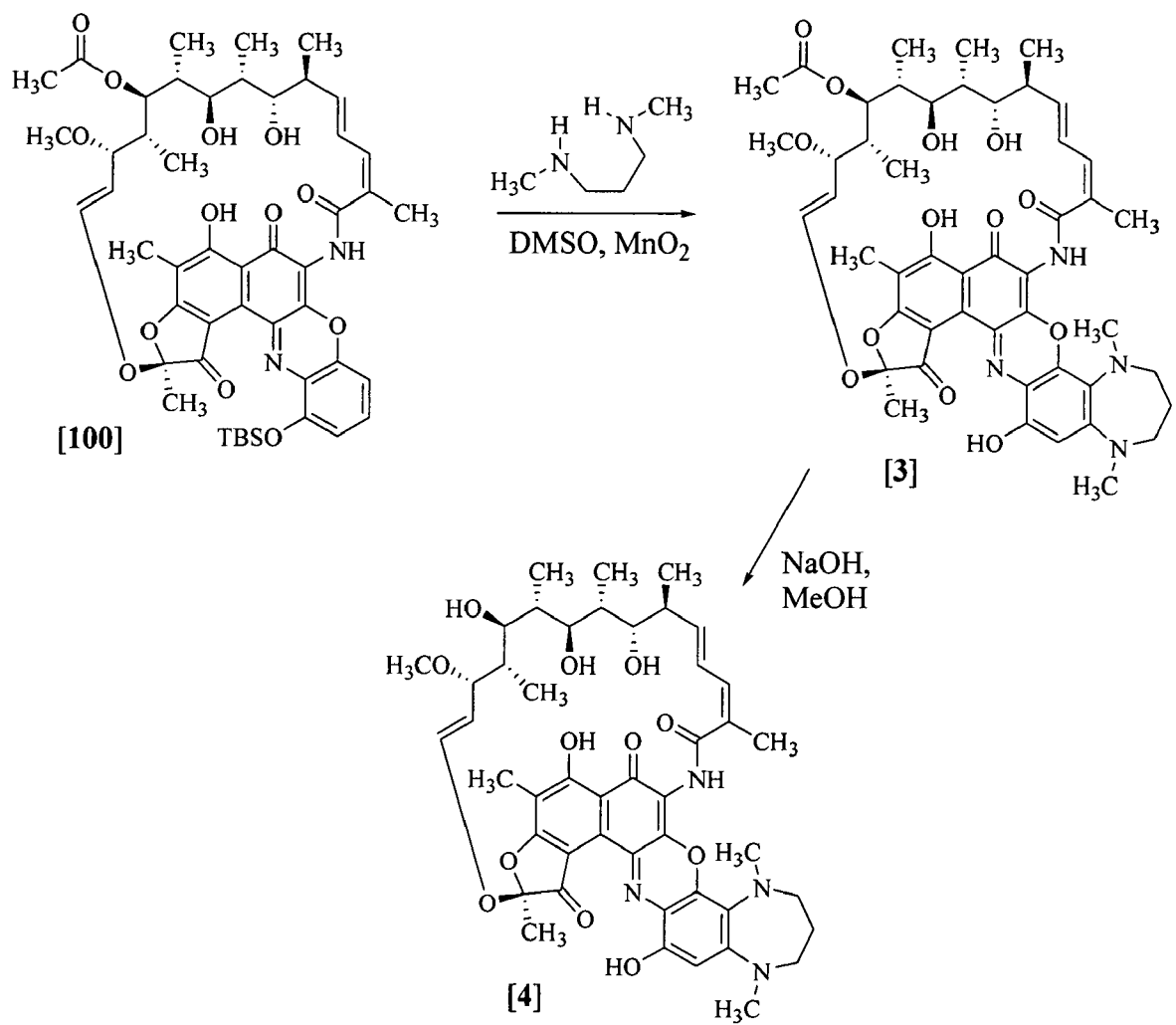
FIG. 6 is a synthetic scheme showing procedures to produce compounds compounds 3 and 4, as described in Examples 6 and 7, respectively.

As shown in FIG. 6, compound 100 (1.03 g, 1.13 mmol), N,N'-dimethyl-1,3-propanediamine (0.5 mL, 4 mmol), and manganese(IV) oxide (503 mg, 5.78 mmol) were stirred at room temperature in methyl sulfoxide (10 mL) for 24 h. The reaction was diluted with methylene chloride and filtered through Celite™. The resulting solution washed with water (3×) and dried over sodium sulfate. Filtration, followed by removal of the solvent in vacuo yielded a blue residue that was purified via MPLC (silica gel, gradient 1.5-16.5%, methanol in methylene chloride) to yield compound 3 as a blue solid (420 mg, 0.467 mmol, 41% yield); ESI (+) MS: 899 (M+H$^+$); UV/Vis: $\lambda_{max}$=686.3 nm; Mp 236-240° C.

EXAMPLE 7

Synthesis of Compound 4

As shown in FIG. 6, the title compound was prepared by the general deacetylation procedure of Example 2 using compound 3 (136 mg, 0.151 mmol) to provide, after MPLC purification (silica gel, gradient 2.5-12.5%, methanol in methylene chloride) compound 4 (97 mg, 75% yield) as a blue solid; Mp=225-230° C.; ESI (+) MS: 857 (M+H$^+$); UV/Vis: $\lambda_{max}$=686.0 nm.

EXAMPLE 8

Synthesis of Compound 5

Figure 7:
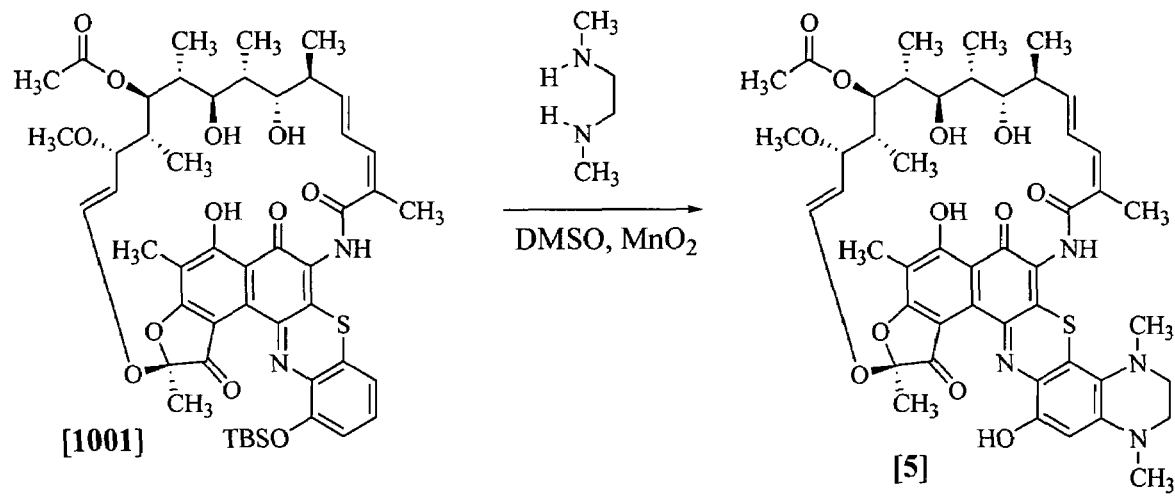
FIG. 7 is a synthetic scheme showing a procedure to produce compound 5 of the present invention, as described in Example 8.

The title compound was prepared as shown in FIG. 7. To a stirred solution of compound 1001 (25 mg, 0.031 mmol) in DMSO (3 mL) was added manganese(IV) oxide (21.6 mg, 0.250 mmol) and N,N'-dimethylethylenediamine (11.1 mg, 0.125 mmol). The resulting suspension was stirred at room temperature for 36 hours. The reaction mixture was diluted with methylene chloride, filtered through Celite™, washed with water (3×), and dried over sodium sulfate. Filtration, followed by removal of the solvent in vacuo, gave a mixture of compounds that were purified by preparative TLC (10% MeOH/CH$_2$Cl$_2$) to yield compound 5 (2.9 mg) as a blue solid; ESI (+) MS: 886 (M+H$^+$).

EXAMPLE 9

Synthesis of Compound 6

Figure 8:
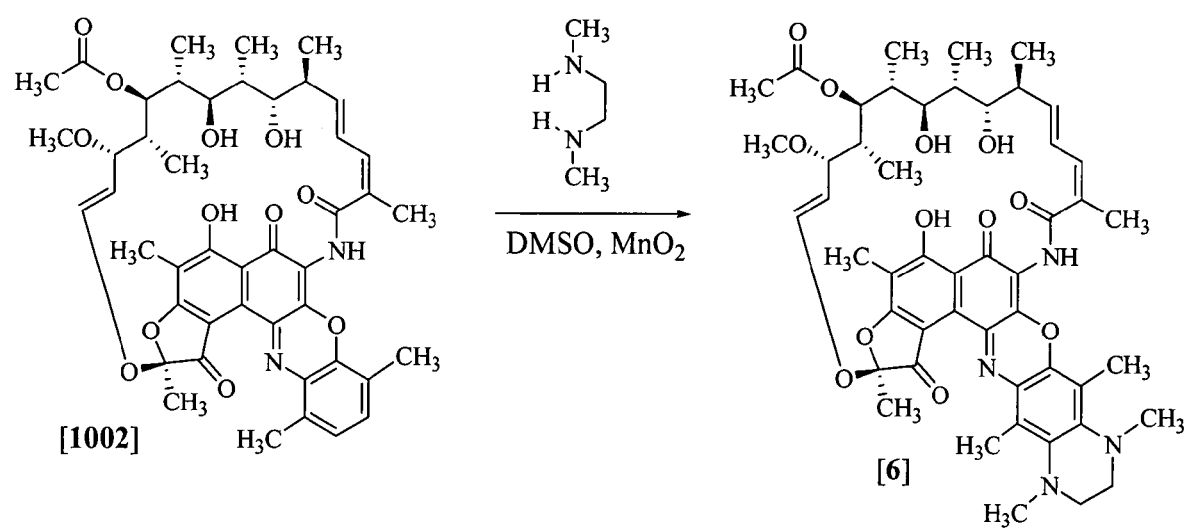
FIG. 8 is a synthetic scheme showing a procedure to produce compound 6 of the present invention, as described in Example 9.

The title compound was prepared as shown in FIG. 8. To a stirred solution of compound 1002 (81 mg, 0.1 mmol) in DMSO (10 mL) was added manganese(IV) oxide (69 mg, 0.8 mmol) and N,N'-dimethylethylenediamine (35 mg, 0.4 mmol), and the resulting suspension was stirred at RT for 36 hours. The reaction was diluted with methylene chloride and filtered through Celite™. The resulting solution washed with water (3×), and dried over sodium sulfate. Filtration, followed by removal of the solvent in vacuo, gave a mixture of compounds that were purified by preparative TLC (10% MeOH/CH$_2$Cl$_2$) to yield compound 6 (1.0 mg); ESI (+) MS: 898 (M+H$^+$).

EXAMPLE 10

Synthesis of Compound 7

Figure 9:
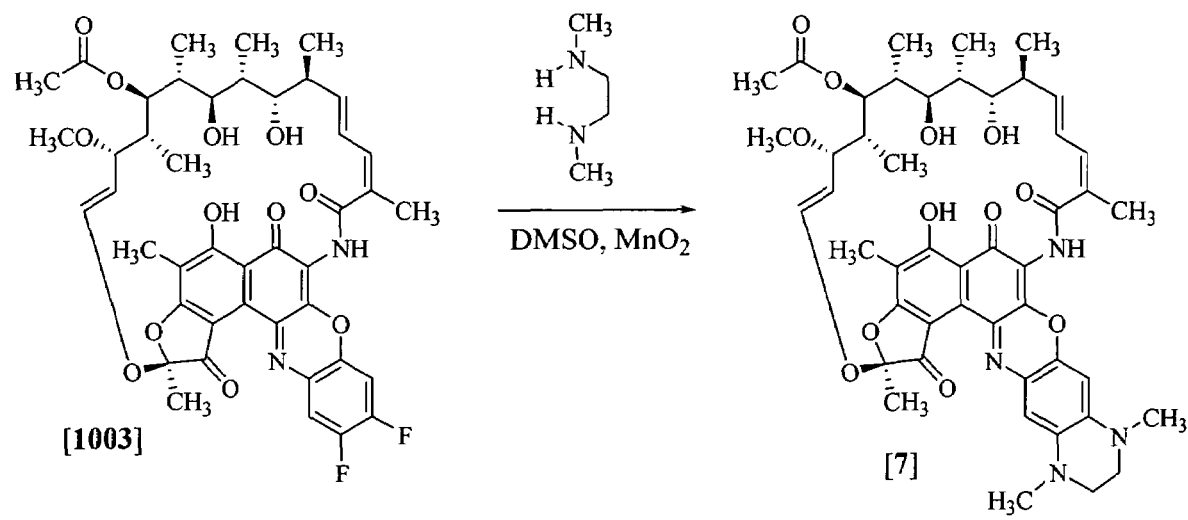
FIG. 9 is a synthetic scheme showing a procedure to produce compound 7 of the present invention, as described in Example 10.

The title compound was prepared as shown in FIG. 9. To a stirred solution of compound 1003 (82 mg, 0.1 mmol) in DMSO (5 mL) was added manganese(IV) oxide (69 mg, 0.8 mmol) and N,N'-dimethylethylenediamine (35 mg, 0.4 mmol), and the resulting suspension was stirred at RT for 36 hours. The reaction was diluted with methylene chloride and filtered through Celite™. The resulting solution washed with water (3×), and dried over sodium sulfate. Filtration, followed by removal of the solvent in vacuo, yielded the mixture which was purified by silica gel column (10% MeOH/CH$_2$Cl$_2$) to yield the product as a green solid, which was purified further by preparative TLC (10% MeOH/CH$_2$Cl$_2$) to yield compound 7 (3.0 mg); ESI (+) MS: 870 (M+H$^+$).

EXAMPLE 11

Synthesis of Compound 8

Figure 10:
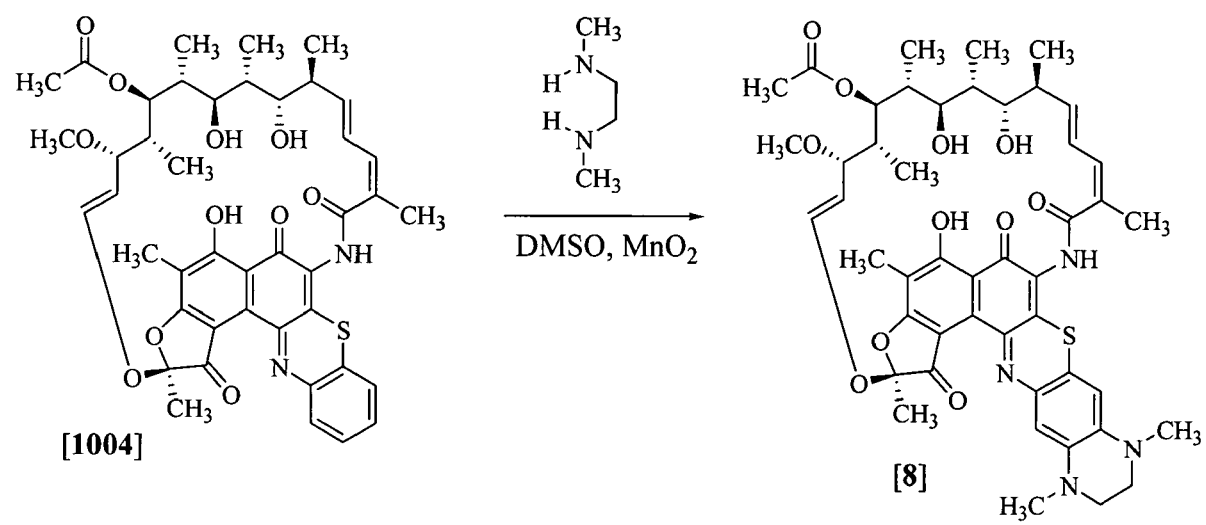
FIG. 10 is a synthetic scheme showing a procedure to produce compound 8 of the present invention, as described in Example 11.

The title compound was prepared as shown in FIG. 10. To a stirred solution of compound 1004 (25 mg, 0.031 mmol) in DMSO (3 mL) was added manganese(IV) oxide (21.6 mg, 0.250 mmol) and N,N'-dimethylethylenediamine (11.1 mg, 0.125 mmol), and the resulting suspension was stirred at RT for 36 hours. The reaction was diluted with methylene chloride and filtered through Celite™. The resulting solution washed with water (3×), and dried over sodium sulfate. Filtration, followed by removal of the solvent in vacuo, yielded a mixture of compounds which were purified by preparative TLC (10% MeOH/CH$_2$Cl$_2$) to yield compound 8 as a blue solid (2.9 mg); ESI (+) MS: 886 (M+H$^+$).

EXAMPLE 12

MIC Assay

MICs of candidate compounds of the invention can be determined, for example, by the method of Lee et al., *Am. Rev. Respir. Dis.* 136:349, 1987. To a BACTEC 12B vial (4 mL of 7H12B medium), 0.1 mL of a 10-fold dilution of subculture of the test organisms in 7H9 medium (optical density at 540 nm, 0.1) is inoculated and cultured at 37° C. until a growth index (GI) of 999 is reached. Then the broth culture is removed and diluted 100-fold, and 0.1 mL of the dilution is inoculated into a BACTEC 12B vial with or without a candidate compound. The candidate compound containing vials can hold 0.1 mL of candidate compound solution appropriately diluted to obtain the desired concentration. A 1% control vial, 0.1 mL of the 100-fold dilution of the inoculum described above, is inoculated into 12B vial without candidate compound. The 12B vials are incubated at 37° C., and GI readings recorded daily, using a BACTEC 460 TB instrument (Johnston Laboratories, Townsend, Md.), until the control vial reaches a GI greater than 30. When the final readings in the GI of the candidate containing vials are lower than those of the 1% control, the drug is considered to have inhibited more than 99% of the bacterial population, and this concentration will be defined as the MIC.

Table 1 gives structures and MIC values for some of the compounds of the invention.

TABLE 1

Structures and MIC values

| Cmpd. No. | Structure* | Formula | MP (° C.) | MW | MIC (µg/mL) | | | | | |
|---|---|---|---|---|---|---|---|---|---|---|
| | | | | | C. trachomatis | S. aureus | S. pneumo. | E. faecalis | H. flu | E. coli |
| 1 | A, CH$_3$/CH$_3$, HO | C$_{47}$H$_{56}$N$_4$O$_{13}$ | 276-7 | 884.974 | 6.4 × 10$^{-5}$ | 0.008 | 0.00012 | 1 | 1 | 8 |
| 2 | B, CH$_3$/CH$_3$, HO | C$_{45}$H$_{54}$N$_4$O$_{12}$ | 234-40 | 842.938 | 0.001 | 0.5 | 0.06 | 1 | 2 | 8 |
| 3 | A, H$_3$C/H$_3$C, HO | C$_{48}$H$_{58}$N$_4$O$_{13}$ | 236-40 | 899.001 | 6.4 × 10$^{-5}$ | 0.06 | 0.008 | 4 | 2 | >8 |
| 4 | B, H$_3$C/H$_3$C, HO | C$_{46}$H$_{56}$N$_4$O$_{12}$ | 225-30 | 856.964 | 0.001 | 0.12 | 0.00012 | 1 | 2 | >8 |

TABLE 1-continued
Structures and MIC values
| Cmpd. No. | Structure* | Formula | MP (° C.) | MW | MIC (µg/mL) | | | | | |
|---|---|---|---|---|---|---|---|---|---|---|
| | | | | | C. trachomatis | S. aureus | S. pneumo. | E. faecalis | H. flu | E. coli |
| 5 | 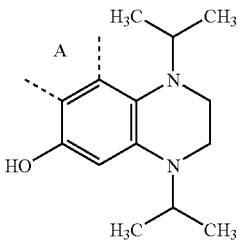 | $C_{51}H_{64}N_4O_{13}$ | | 941.082 | 0.01 | 0.06 | 0.008 | 4 | 2 | >8 |
| 6 | 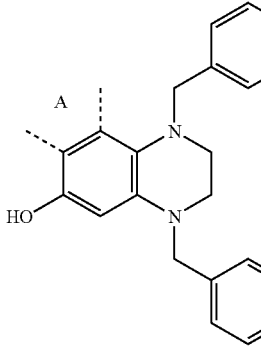 | $C_{59}H_{64}N_4O_{13}$ | | 1037.17 | 2 | 0.12 | 8 | >8 | >8 | |
*A and B represent the following moieties:
A is
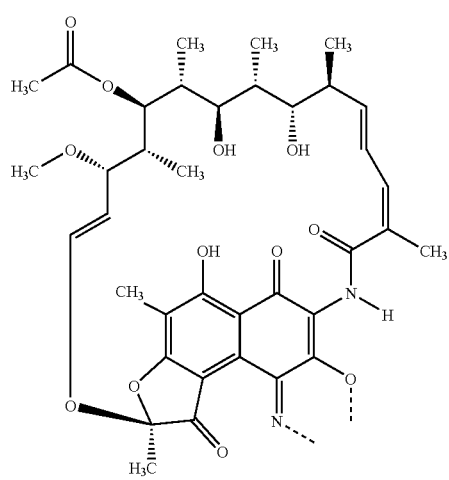

TABLE 1-continued

Structures and MIC values

| | | | | | MIC (μg/mL) | | | | | |
|---|---|---|---|---|---|---|---|---|---|---|
| Cmpd. No. | Structure* | Formula | MP (° C.) | MW | C. trachomatis | S. aureus | S. pneumo. | E. faecalis | H. flu | E. coli | and B is

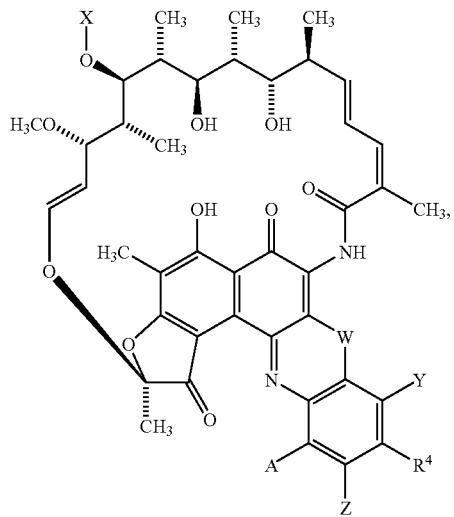

All publications, patent applications, and patents cited in this specification are herein incorporated by reference as if each individual publication, patent application, or patent were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

While the invention has been described in connection with specific embodiments, it will be understood that it is capable of further modifications. Therefore, this application is intended to cover any variations, uses, or adaptations of the invention that follow, in general, the principles of the invention, including departures from the present disclosure that come within known or customary practice within the art.

Other embodiments are within the claims.

What is claimed is:

1. A compound having the formula:

(I)

or a pharmaceutically acceptable salt thereof, wherein (a) A is H, OH, O—($C_1$-$C_6$ alkyl), O—($C_1$-$C_4$ alkaryl), O—($C_6$-$C_{12}$ aryl), O—($C_1$-$C_9$ heteroaryl), or O—($C_1$-$C_4$ alkheteroaryl);

W is O, S, or $NR^1$, wherein $R^1$ is H, $C_1$-$C_6$ alkyl, $C_1$-$C_4$ alkaryl, or $C_1$-$C_4$ alkheteroaryl;

X is H or $COR^2$, wherein $R^2$ is $C_1$-$C_6$ alkyl, which can be substituted with 1-5 OH groups, O—($C_3$-$C_7$ alkyl), which can be substituted with 1-4 OH groups, $C_6$-$C_{12}$ aryl, $C_1$-$C_4$ alkaryl, $C_1$-$C_9$ heteroaryl, or $C_1$-$C_4$ alkheteroaryl, wherein each alkyl carbon is bound to no more than one oxygen atom;

Y is H, Hal, or $OR^3$, wherein $R^3$ is $C_1$-$C_6$ alkyl, $C_6$-$C_{12}$ aryl, $C_1$-$C_4$ alkaryl, $C_1$-$C_9$ heteroaryl, or $C_1$-$C_4$ alkheteroaryl;

$R^4$ is $OR^5$, or $SR^5$, wherein $R^5$ is defined below in relation to $R^7$; and Z is $(CR^{11}R^{12})_n NR^7 R^8$, wherein n is 0 or 1, $R^7$ and $R^5$ together represent a bond or form a substituted or unsubstituted $C_1$-$C_4$ linkage, $R^8$ is H, $C_1$-$C_6$ alkyl, $C_6$-$C_{12}$ aryl, $C_1$-$C_4$ alkaryl, $C_1$-$C_9$ heteroaryl, or $C_1$-$C_4$ alkheteroaryl, $COR^{10}$, $CO_2R^{10}$, $CONHR^{10}$, $CSR^{10}$, $COSR^{10}$, $CSOR^{10}$, $CSNHR^{10}$, $SO_2R^{10}$, or $SO_2NHR^{10}$, wherein $R^{10}$ is $C_1$-$C_6$ alkyl, $C_6$-$C_{12}$ aryl, $C_1$-$C_4$ alkaryl, $C_1$-$C_9$ heteroaryl, or $C_1$-$C_4$ alkheteroaryl, or $R^8$ does not exist and a double bond is formed between N and an $R^5$-$R^7$ $C_1$ carbon linkage, each of $R^{11}$ and $R^{12}$ is, independently, H, $C_1$-$C_6$ alkyl, $C_1$-$C_4$ alkaryl, or $C_1$-$C_4$ alkheteroaryl, or $R^{12}$ does not exist and a double bond is formed between N and the carbon bearing $R^{11}$;

or (b) A is H, OH, O—($C_1$-$C_6$ alkyl), O—($C_1$-$C_4$ alkaryl), O—($C_6$-$C_{12}$ aryl), O—($C_1$-$C_9$ heteroaryl), or O—($C_1$-$C_4$ alkheteroaryl);

W is O, S, or $NR^1$, wherein $R^1$ is H, $C_1$-$C_6$ alkyl, $C_1$-$C_4$ alkaryl, or $C_1$-$C_4$ alkheteroaryl;

X is H or COR$^2$, wherein R$^2$ is C$_1$-C$_6$ alkyl, which can be substituted with 1-5 OH groups, O—(C$_3$-C$_7$ alkyl), which can be substituted with 1-4 OH groups, C$_6$-C$_{12}$ aryl, C$_1$-C$_4$ alkaryl, C$_1$-C$_9$ heteroaryl, or C$_1$-C$_4$ alkheteroaryl, wherein each alkyl carbon is bound to no more than one oxygen atom;

Z is H, Hal, or OR$^3$, wherein R$^3$ is C$_1$-C$_6$ alkyl, C$_6$-C$_{12}$ aryl, C$_1$-C$_4$ alkaryl, C$_1$-C$_9$ heteroaryl, or C$_1$-C$_4$ alkheteroaryl;

R$^4$ is OR$^5$, SR$^5$, or NR$^5$R$^6$, wherein R$^5$ is defined below in relation to R$^7$ and R$^6$ is H, C$_1$-C$_6$ alkyl, C$_6$-C$_{12}$ aryl, C$_1$-C$_4$ alkaryl, C$_1$-C$_9$ heteroaryl, or C$_1$-C$_4$ alkheteroaryl, COR$^9$, CO$_2$R$^9$, CONHR$^9$, CSR$^9$, COSR$^9$, CSOR$^9$, CSNHR$^9$, SO$_2$R$^9$, or SO$_2$NHR$^9$, wherein R$^9$ is C$_1$-C$_6$ alkyl, C$_6$-C$_{12}$ aryl, C$_1$-C$_4$ alkaryl, heteroaryl, or C$_1$-C$_4$ alkheteroaryl; and Y is (CR$^{11}$R$^{12}$)$_n$NR$^7$R$^8$, wherein n is 0 or 1, R$^7$ and R$^5$ together represent a bond or form a substituted or unsubstituted C$_1$-C$_4$ linkage, R$^8$ is H, C$_1$-C$_6$ alkyl, C$_6$-C$_{12}$ aryl, C$_1$-C$_4$ alkaryl, C$_1$-C$_9$ heteroaryl, or C$_1$-C$_4$ alkheteroaryl, COR$^{10}$, CO$_2$R$^{10}$, CONHR$^{10}$, CSR$^{10}$, COSR$^{10}$, CSOR$^{10}$, CSNHR$^{10}$, SO$_2$R$^{10}$, or SO$_2$NHR$^{10}$, wherein R$^{10}$ is C$_1$-C$_6$ alkyl, C$_6$-C$_{12}$ aryl, C$_1$-C$_4$ alkaryl, C$_1$-C$_9$ heteroaryl, or C$_1$-C$_4$ alkheteroaryl, or R$^8$ does not exist and a double bond is formed between N and an R$^5$-R$^7$ C$_1$ carbon linkage, each of R$^{11}$ and R$^{12}$ is, independently, H, C$_1$-C$_6$ alkyl, C$_1$-C$_4$ alkaryl, or C$_1$-C$_4$ alkheteroaryl, or R$^{12}$ does not exist and a double bond is formed between N and the carbon bearing R$^{11}$, wherein the C$_1$-C$_9$ heteroaryl is selected from the group consisting of furanyl, thienyl, pyrrolyl, imidazolyl, pyrazolyl, oxazolyl, isoxazolyl, thiazolyl, isothiazolyl, triazolyl, tetrazolyl, oxadiazolyl, oxatriazolyl, pyridyl, pyridazyl. pyrimidyl, pyrazyl, triazyl, benzofuranyl, isobenzofuranyl, benzothienyl, indole, indazolyl, indolizinyl, benzisoxazolyl, quinolinyl, isoquinolinyl, cinnolinyl, quinazolinyl, naphtyridinyl, phthalazinyl, phenanthrolinyl, purinyl, and carbazolyl.

2. The compound of claim 1, wherein (a) A is H, OH, O—(C$_1$-C$_6$ alkyl), O—(C$_1$-C$_4$ alkaryl);

W is O, S, or NR$^1$, wherein R$^1$ is H or C$_1$-C$_6$ alkyl;

X is H or COR$^2$, wherein R$^2$ is C$_1$-C$_6$ alkyl, which can be substituted with from 1 to 5 OH groups, or O—(C$_3$-C$_7$ alkyl), which can be substituted with from 1 to 4 OH groups, wherein each alkyl carbon is bound to no more than one oxygen atom;

Y is H, Hal, or OR$^3$, wherein R$^3$ is C$_1$-C$_6$ alkyl or C$_1$-C$_4$ alkaryl;

R$^4$ is OR$^5$ or SR$^5$, wherein R$^5$ is defined below in relation to R$^7$; and Z is (CR$^{11}$R$^{12}$)$_n$NR$^7$R$^8$, wherein n is 0 or 1, R$^7$ and R$^5$ together represent a bond or form a substituted or unsubstituted C$_1$-C$_4$ linkage, R$^8$ is H, C$_1$-C$_6$ alkyl, C$_1$-C$_4$ alkaryl, COR$^{10}$, CO$_2$R$^{10}$, CONHR$^{10}$, CSR$^{10}$, COSR$^{10}$, CSOR$^{10}$, CSNHR$^{10}$, SO$_2$R$^{10}$, or SO$_2$NHR$^{10}$, wherein R$^{10}$ is C$_1$-C$_6$ alkyl, C$_6$-C$_{12}$ aryl, C$_1$-C$_4$ alkaryl, heteroaryl, or C$_1$-C$_4$ alkheteroaryl, or R$^8$ does not exist and a double bond is formed between N and an R$^5$-R$^7$ C$_1$ carbon linkage, each of R$^{11}$ and R$^{12}$ is, independently, H, C$_1$-C$_6$ alkyl, C$_1$-C$_4$ alkaryl, or C$_1$-C$_4$ alkheteroaryl, or R$^{12}$ does not exist and a double bond is formed between N and the carbon bearing R$^{11}$;

or (b) A is H, OH, O—(C$_1$-C$_6$ alkyl), or O—(C$_1$-C$_4$ alkaryl);

W is O, S, or NR$^1$, wherein R$^1$ is H, or C$_1$-C$_6$ alkyl;

X is H or COR$^2$, wherein R$^2$ is C$_1$-C$_6$ alkyl, which can be substituted with from 1 to 5 OH groups, O—(C$_3$-C$_7$ alkyl), which can be substituted with from 1 to 4 OH groups, wherein each alkyl carbon is bound to no more than one oxygen atom;

Z is H, Hal, or OR$^3$, wherein R$^3$ is C$_1$-C$_6$ alkyl, or C$_1$-C$_4$ alkaryl;

R$^4$ is OR$^5$, SR$^5$, or NR$^5$R$^6$, wherein R$^5$ is defined below in relation to R$^7$ and R$^6$ is H, C$_1$-C$_6$ alkyl, C$_1$-C$_4$ alkaryl, COR$^9$, CO$_2$R$^9$, CONHR$^9$, CSR$^9$, COSR$^9$, CSOR$^9$, CSNHR$^9$, SO$_2$R$^9$, or SO$_2$NHR$^9$, wherein R$^9$ is C$_1$-C$_6$ alkyl, C$_6$-C$_{12}$ aryl, C$_1$-C$_4$ alkaryl, heteroaryl, or C$_1$-C$_4$ alkheteroaryl; and Y is (CR$^{11}$R$^{12}$)$_n$ NR$^7$R$^8$, wherein n is 0 or 1, R$^7$ and R$^5$ together represent a bond or form a substituted or unsubstituted C$_1$-C$_4$ linkage, R$^8$ is H, C$_1$-C$_6$ alkyl, C$_1$-C$_4$ alkaryl, COR$^{10}$, CO$_2$R$^{10}$, CONHR$^{10}$, CSR$^{10}$, COSR$^{10}$, CSOR$^{10}$, CSNHR$^{10}$, SO$_2$R$^{10}$, or SO$_2$NHR$^{10}$, wherein R$^{10}$ is C$_1$-C$_6$ alkyl, C$_6$-C$_{12}$ aryl, C$_1$-C$_4$ alkaryl, heteroaryl, or C$_1$-C$_4$ alkheteroaryl, or R$^8$ does not exist and a double bond is formed between N and an R$^5$-R$^7$ C$_1$ carbon linkage, each of R$^{11}$ and R$^{12}$ is, independently, H, C$_1$-C$_6$ alkyl, C$_1$-C$_4$ alkaryl, or C$_1$-C$_4$ alkheteroaryl, or R$^{12}$ does not exist and a double bond is formed between N and the carbon bearing R$^{11}$, wherein heteroaryl is selected from the group consisting of furanyl, thienyl, pyrrolyl, imidazolyl, pyrazolyl, oxazolyl, isoxazolyl, thiazolyl, isothiazolyl, triazolyl, tetrazolyl, oxadiazolyl, oxatriazolyl, pyridyl, pyridazyl, pyrimidyl, pyrazyl, triazyl, benzofuranyl, isobenzofuranyl, benzothienyl, indole, indazolyl, indolizinyl, benzisoxazolyl, quinolinyl, isoquinolinyl, cinnolinyl, quinazolinyl, naphtyridinyl, phthalazinyl, phenanthrolinyl, purinyl, and carbazolyl.

3. The compound of claim 1, wherein said compound of formula I is selected from a group consisting of:

(a) the compound wherein A is OH, X is COCH$_3$, W is O, Z is H, and Y and R$^4$ together are

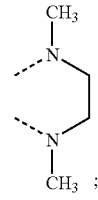

(b) the compound wherein A is OH, X is H, W is O, Z is H, and Y and Y and R$^4$ together are

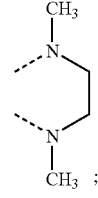

(c) the compound wherein A is OH, X is COCH₃, W is O, Z is H, and Y and R⁴ together are

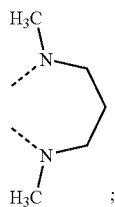

(d) the compound wherein A is OH, X is H, W is O, Z is H, and Y and R⁴ together are

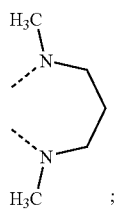

(e) the compound wherein A is OH, X is COCH₃, W is O, Z is H, and Y and R⁴ together are

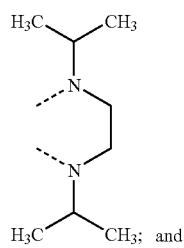

and (f) the compound wherein A is OH, X is COCH₃, W is O, Z is H, and Y and R⁴ together are

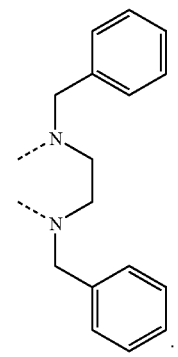

4. A pharmaceutical composition comprising a pharmaceutically acceptable carrier or diluent and the compound of claim 1.

5. A method of treating a Gram positive bacterial infection or a condition caused by a Gram positive bacterial infection in an animal, said method comprising administering to said animal the compound of claim 1 in an amount sufficient to treat said infection or said condition.

6. The method of claim 5, wherein said compound is administered orally, topically, intravenously, intramuscularly, or subcutaneously.

7. The method of claim 5, wherein said animal is a human.

8. The method of claim 5, wherein said condition is selected from the group consisting of community-acquired pneumonia, upper and lower respiratory tract infections, skin and soft tissue infections, bone and joint infections, and hospital-acquired lung infections.

9. The method of claim 5, wherein said infection is a persistent infection.

10. The method of claim 5, wherein said infection is an ear infection.

11. The method of claim 5, wherein said microbial infection is an intracellular infection.

12. The method of claim 5, wherein said infection is caused by a Gram positive coccus.

13. The method of claim 5, wherein said infection is caused by *N. gonorrhoeae*.

14. The method of claim 5, wherein said infection is caused by *C. difficile*.

15. The method of claim 5, wherein said infection is caused by *C. pneumoniae*.

16. The method of claim 5, wherein said infection is caused by *H. pylori*.

17. The method of claim 16, wherein said method further comprises administering to said animal a proton pump inhibitor or bismuth preparation.

18. The method of claim 5, wherein said Gram positive bacterial infection is caused by a bacterium selected from the group consisting of *Anaplasma bovis, A. caudatum, A. centrale, A. marginale A. ovis, A. phagocytophila, A. platys, Bartonella bacilliformis, B. clarridgeiae, B. elizabethae, B. henselae, B. henselae phage, B. quintana, B. taylorii, B. vinsonii, Borrelia afzelii, B. andersonii, B. anserina, B. bissettii, B. burgdorferi, B. crocidurae, B. garinii, B. hermsii, B. japonica, B. miyamotoi, B. parkeri, B. recurrentis, B. turdi, B. turicatae, B. valaisiana, Brucella abortus, B. melitensis, C. psittaci, C. trachomatis, Cowdria ruminantium, Coxiella burnetii, Ehrlichia canis, E. chaffeensis, E. equi, E. ewingii, E. muris, E. phagocytophila, E. platys, E. risticii, E. ruminantiurn, E. sennetsu,Haernobartonella canis, H felis, H muris, Mycoplasma anthriditis, M buccale, Ml faucium, Ml fermentans, M genitalium, M hominis, M laidlawii, M lipophilum, M orale, M penetrans, M pirum, M pneumoniae, M salivarium, M spermatophilum, Rickettsia australis, R. conorii, R. felis, R. helvetica, R. japonica, R. massiliae, R. montanensis, R. peacockii, R. prowazekii, R. rhipicephali, R. rickettsii, R. sibirica*, and *R. typhi*.

19. The method of claim 5, wherein said method further comprises administering to said animal a second agent selected from the group consisting of: antifungal agent, antiviral agent, antibacterial agent, and antiprotozoan agent.

20. The method of claim 5, wherein said condition is selected from the group consisting of community-acquired pneumonia, upper and lower respiratory tract infections, skin and soft tissue infections, bone and joint infections, nosocomial associated diarrhea, antibacterial-associated bacterial diarrhea, *C. difficile* associated diarrhea, and hospital-acquired infections.

21. The method of claim 5, wherein said infection is caused by any one of the following: *Chlamydia* spp. (e.g., *C. trachomatis, C. pneumoniae, C. psittaci, C. suis, C. pecorum, C. abortus, C. caviae, C. felis, C. muridarum*), *N. hartmannellae, W. chondrophila, S. nevegensis*, or *P. acanthamoeba*.

* * * * *

UNITED STATES PATENT AND TRADEMARK OFFICE
CERTIFICATE OF CORRECTION

PATENT NO. : 7,494,991 B2 Page 1 of 1
APPLICATION NO. : 11/804141
DATED : February 24, 2009
INVENTOR(S) : John H. Van Duzer It is certified that error appears in the above-identified patent and that said Letters Patent is hereby corrected as shown below:

Column 30, line 33: "solution washed" should be -- solution was washed --.
Column 31, lines 1-2: "solution washed" should be -- solution was washed --.
Column 36, line 39 (claim 1): "is bound to" should be -- is bonded to --.
Column 37, line 27 (claim 1): "between N and an" should be -- between N and a --.
Column 38, line 57 (claim 3): "and Y and Y" should be -- and Y --.

Signed and Sealed this

Twenty-first Day of April, 2009

JOHN DOLL
*Acting Director of the United States Patent and Trademark Office*